(12) United States Patent
Anantaneni et al.

(10) Patent No.: US 10,669,228 B2
(45) Date of Patent: Jun. 2, 2020

(54) PREPARATION OF NEW STABLE HYDROGEN SULFIDE SCAVENGERS USEFUL IN BOTH WATER AS WELL AS OIL MEDIUM APPLICATIONS

(71) Applicant: ECOLAB USA INC., St. Paul, MN (US)

(72) Inventors: Prakasa Rao Anantaneni, Richmond, TX (US); Ryan Matthew Harrington, Houston, TX (US); David Tarverdi, Riverside, IL (US); Lawrence J. Karas, Missouri City, TX (US); Ravindranath Mukkamala, Sugar Land, TX (US); Subhasis De, Houston, TX (US)

(73) Assignee: ECOLAB USA INC., St. Paul, MN (US)

( * ) Notice: Subject to any disclaimer, the term of this patent is extended or adjusted under 35 U.S.C. 154(b) by 0 days.

(21) Appl. No.: 16/559,926

(22) Filed: Sep. 4, 2019

(65) Prior Publication Data
US 2020/0031759 A1    Jan. 30, 2020

Related U.S. Application Data

(62) Division of application No. 15/717,338, filed on Sep. 27, 2017, now Pat. No. 10,442,755.

(Continued)

(51) Int. Cl.
*C07C 217/42*    (2006.01)
*C07C 211/13*    (2006.01)
(Continued)

(52) U.S. Cl.
CPC ........ *C07C 217/28* (2013.01); *B01D 19/0005* (2013.01); *B01D 53/52* (2013.01); *C02F 1/683* (2013.01); *C10G 21/20* (2013.01); *C10G 29/20* (2013.01); *C10L 3/103* (2013.01); *C02F 2101/101* (2013.01); *C10G 2300/207* (2013.01); *C10L 2290/545* (2013.01)

(58) Field of Classification Search
None
See application file for complete search history.

(56) References Cited

U.S. PATENT DOCUMENTS 6,024,866 A * 2/2000 Weers ............... C10L 1/221
                                                208/236
7,264,786 B2    9/2007 Pakulski et al.
(Continued)

OTHER PUBLICATIONS

International Search Report and Written Opinion for PCT/US2017/053680, 15 pages (dated Dec. 19, 2017).
(Continued)

*Primary Examiner* — Daniel Berns
(74) *Attorney, Agent, or Firm* — Eric D. Babych; Barnes & Thornburg LLP

(57) ABSTRACT

The disclosure provides compositions and methods that are useful in removing, lowering, or otherwise controlling hydrogen sulfide and mercaptans. The compositions and methods can be used in any industry where hydrogen sulfide poses problems, such as when dealing with crude oil based, natural gas based, and/or coal based products. In some embodiments, the compositions include one or more alkoxylated amino formaldehyde adducts.

5 Claims, 11 Drawing Sheets

Related U.S. Application Data

(60) Provisional application No. 62/402,544, filed on Sep. 30, 2016.

(51) Int. Cl.
| | | |
|---|---|---|
| *C07C 211/14* | (2006.01) | |
| *C07C 215/12* | (2006.01) | |
| *C07C 215/14* | (2006.01) | |
| *C07C 215/18* | (2006.01) | |
| *C10G 29/20* | (2006.01) | |
| *C10G 21/20* | (2006.01) | |
| *C10L 3/10* | (2006.01) | |
| *C02F 1/68* | (2006.01) | |
| *B01D 53/52* | (2006.01) | |
| *C07C 217/28* | (2006.01) | |
| *B01D 19/00* | (2006.01) | |
| *C02F 101/10* | (2006.01) | |

(56) References Cited

U.S. PATENT DOCUMENTS

| | | |
|---|---|---|
| 10,442,755 B2 * | 10/2019 | Anantaneni ............ C10L 3/103 |
| 2009/0065445 A1 | 3/2009 | Westlund et al. |
| 2012/0329930 A1 | 12/2012 | Stark et al. |

OTHER PUBLICATIONS

Marakhovskii, L.F., et al., "On the Use of Ethylenediamine to Remove Hydrogen Sulfide from Coke Oven Gas," Koks i Khimiya, No. 3, XP055429359, 7 pages (1983).

* cited by examiner

PREPARATION OF NEW STABLE HYDROGEN SULFIDE SCAVENGERS USEFUL IN BOTH WATER AS WELL AS OIL MEDIUM APPLICATIONS

BACKGROUND

1. Field of the Invention

The present disclosure generally relates to removal of contaminants in liquid mediums. More particularly, the disclosure relates to hydrogen sulfide scavengers for use in either water or oil-based mediums.

2. Description of the Related Art

Hydrogen sulfide is very toxic and poses significant challenges in the oil and gas industry. Removal of hydrogen sulfide from liquid or gaseous hydrocarbon streams is also a problem that poses certain safety risks. Many issues associated with hydrogen sulfide are present in drilling, production, transportation, storage, and the processing of crude oil and waste water associated with crude oil. Similar issues arise during the production of natural gas.

The presence of sulfur-containing compounds may result in the deposition of sulfur containing salts, which can cause plugging and corrosion of transmission pipes, valves, regulators, etc. Even flared natural gas needs to be treated to avoid acid rain caused by $SO_2$ formation. Further, in the manufactured gas industry or coke making industry, coal-gas containing unacceptable levels of hydrogen sulfide is commonly produced from destructive distillation of bituminous coal.

Since hydrogen sulfide has an offensive odor and natural gas containing hydrogen sulfide is referred to as "sour" gas, treatments to reduce hydrogen sulfide content are generally referred to as "sweetening" treatments.

BRIEF SUMMARY

In certain embodiments of the present disclosure, methods are provided for treating hydrogen sulfide in a stream, including adding an effective amount of a composition to the stream, wherein the composition comprises a scavenger comprising Formula I:

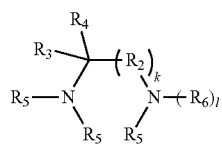

Formula I $k=1-3$, not$=0$
$l=0-3$
provided that when $l=0$ $R_6=R_5$
provided that each N has at most one H

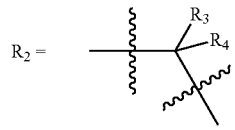

$R_2 =$ $R_3=$H, methyl, ethyl
$R_4=$H, methyl, ethyl
$R_5=$optionally H, $R_7$, or

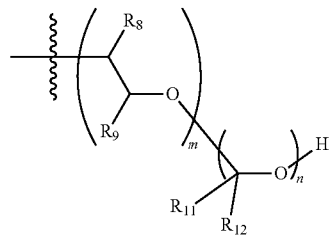

$R_7 =$ 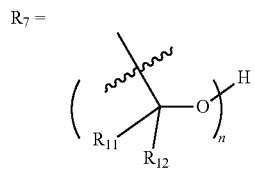

$m=0-4$
provided that when $m=0$, $R_5=$H or $R_7$
$n=0-4$
provided that when $n=0$, the sum of n in formula$>0$
$R_8=$H, methyl, ethyl, propyl
$R_9=$H, methyl, ethyl, propyl, $CH_2OR_{10}$
$R_{10}=$H, methyl, ethyl, propyl, isopropyl, butyl, phenyl, benzyl
$R_{11}=$H, methyl, ethyl
$R_{12}=$H, methyl, ethyl

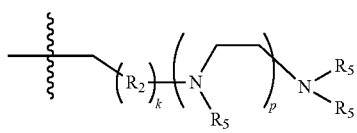

$R_6 =$ $p=0-2$
provided that $l=0, 1$ in Formula I
and reacting the hydrogen sulfide with the scavenger.

In some embodiments, the scavenger comprises a structure selected from the group consisting of:

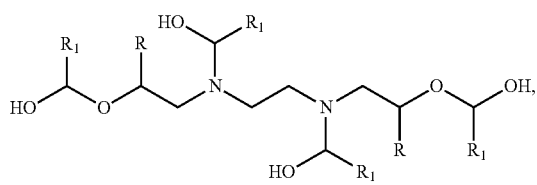

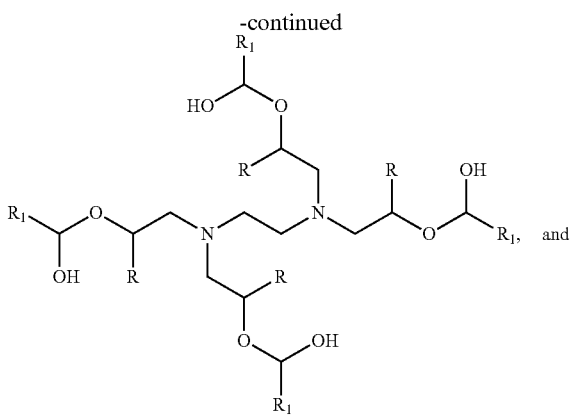

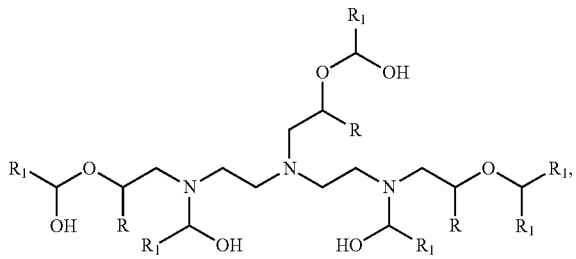

wherein each R is independently selected from a hydrogen, methyl, ethyl, propyl, and/or glycidyl ether ($R_9$=$CH_2OR_{10}$), where $R_{10}$=H, methyl, ethyl, propyl, isopropyl, butyl, phenyl, benzyl; and wherein each $R_1$ is independently selected from a hydrogen or methyl.

In some embodiments, each R and $R_1$ is independently selected from a $C_1$-$C_{14}$ hydrocarbon group or a hydrogen.

In some embodiments, the scavenger comprises a structure selected from the group consisting of:

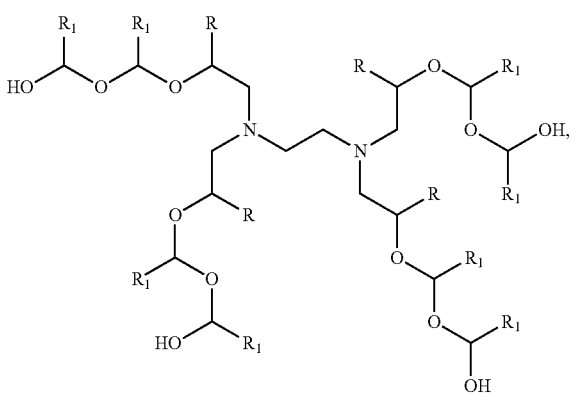

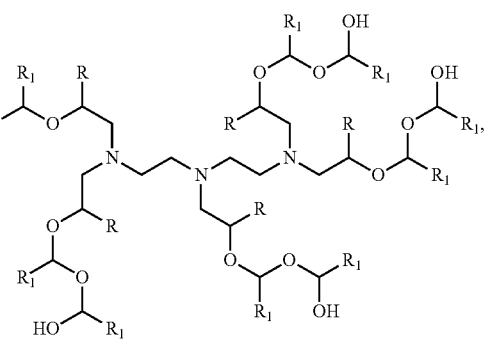

wherein each R is independently selected from a hydrogen, methyl, ethyl, propyl, and/or glycidyl ether ($R_9$=$CH_2OR_{10}$), where $R_{10}$=H, methyl, ethyl, propyl, isopropyl, butyl, phenyl, benzyl; and wherein each $R_1$ is independently selected from a hydrogen or methyl.

In some embodiments, each R and $R_1$ independently comprises a $C_1$-$C_{13}$ hydrocarbon group or a hydrogen.

In some embodiments, the scavenger comprises a structure selected from the group consisting of:

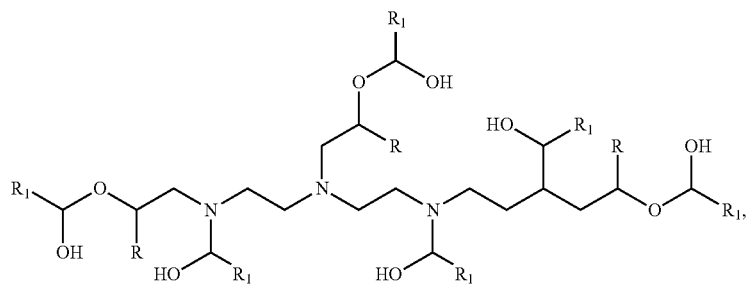

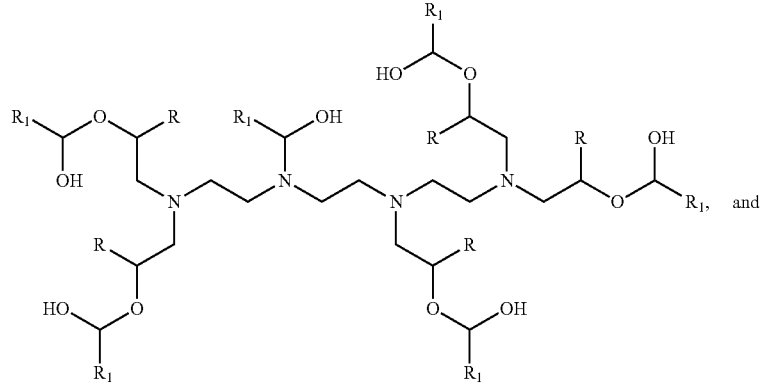

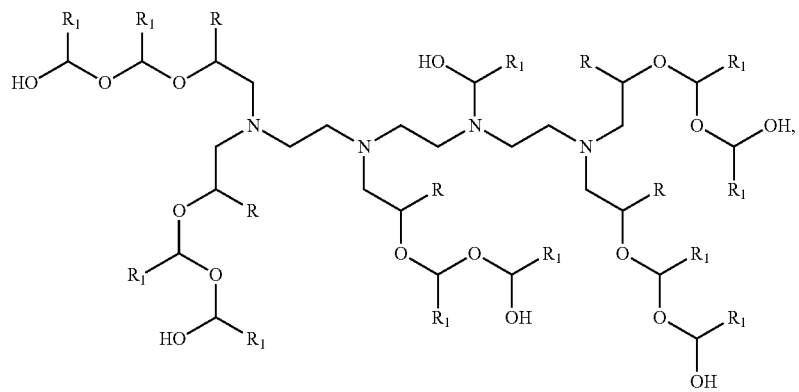

wherein each R is independently selected from a hydrogen, methyl, ethyl, propyl, and/or glycidyl ether ($R_9=CH_2OR_{10}$), where $R_{10}=H$, methyl, ethyl, propyl, isopropyl, butyl, phenyl, benzyl; and wherein each $R_1$ is independently selected from a hydrogen or methyl.

In some embodiments, each R and $R_1$ independently comprise a $C_1$-$C_{14}$ hydrocarbon group or a hydrogen.

In some embodiments, the scavenger comprises a structure selected from the group consisting of

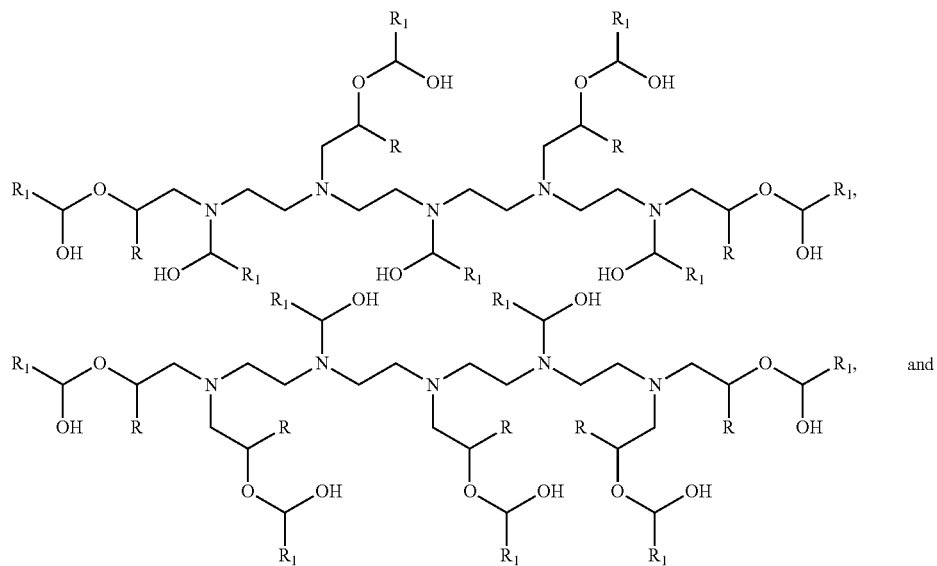

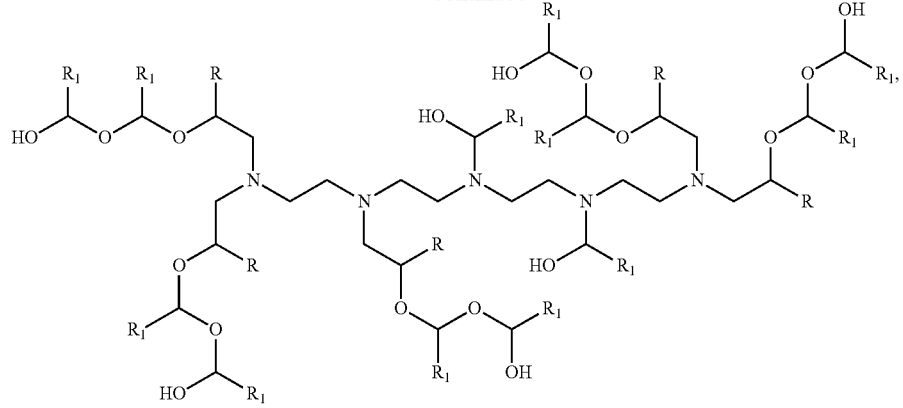

wherein each R is independently selected from a hydrogen, methyl, ethyl, propyl, and/or glycidyl ether ($R_9$=$CH_2OR_{10}$), where $R_{10}$=H, methyl, ethyl, propyl, isopropyl, butyl, phenyl, benzyl; and wherein each $R_1$ is independently selected from a hydrogen or methyl.

In some embodiments, each R and $R_1$ independently comprises a $C_1$-$C_{14}$ hydrocarbon group or a hydrogen.

In some embodiments, the stream is aqueous, gaseous, organic, or any combination thereof.

In some embodiments, the composition is anhydrous.

In some embodiments, the composition comprises an aqueous solvent or an organic solvent.

In certain embodiments, methods are disclosed for treating hydrogen sulfide in a stream, including adding an effective amount of a composition to the stream, wherein the composition includes a scavenger comprising an alkoxylated polyamino aldehyde adduct, wherein the adduct does not comprise a triazine, and reacting the hydrogen sulfide with the scavenger.

In some embodiments, the alkoxylated polyamino aldehyde adduct comprises a structure selected from the group consisting of:

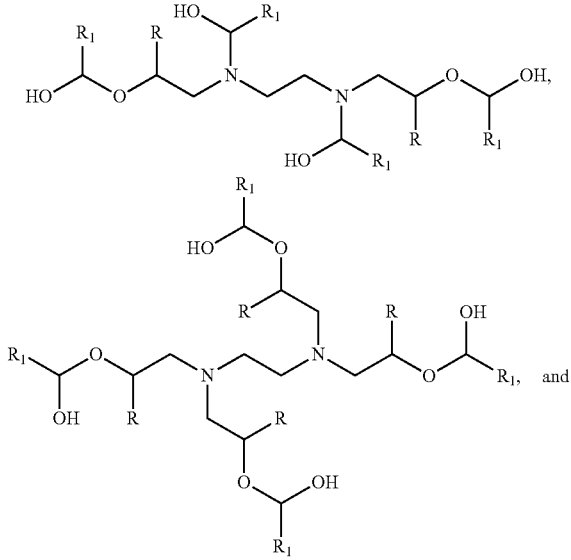

wherein each R is independently selected from a hydrogen, methyl, ethyl, propyl, and/or $CH_2OR_{10}$, where $R_{10}$=H, methyl, ethyl, propyl, isopropyl, butyl, phenyl, benzyl; and wherein each $R_1$ is independently selected from a hydrogen or methyl.

In some embodiments, each R and $R_1$ is independently selected from a $C_1$-$C_{14}$ hydrocarbon group or a hydrogen.

In some embodiments, the alkoxylated polyamino aldehyde adduct comprises a structure selected from the group consisting of

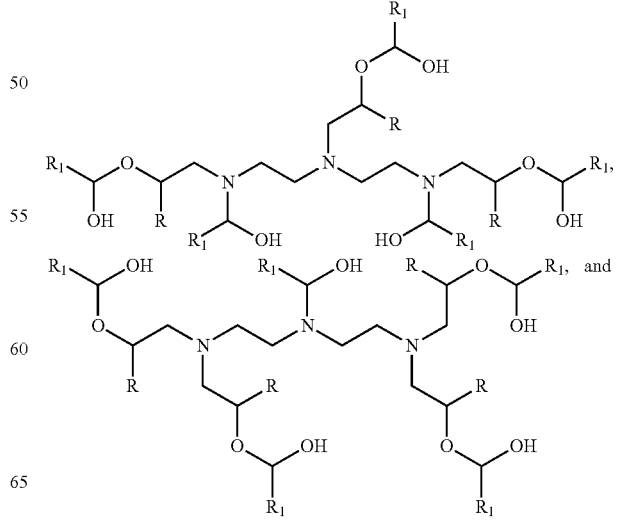

-continued

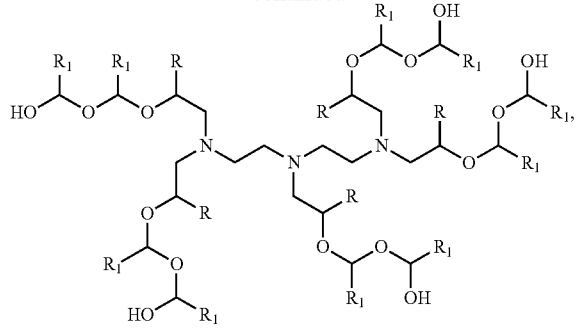

wherein each R is independently selected from a hydrogen, methyl, ethyl, propyl, and/or $CH_2OR_{10}$, where $R_{10}$=H, methyl, ethyl, propyl, isopropyl, butyl, phenyl, benzyl; and wherein each $R_1$ is independently selected from a hydrogen or methyl.

In some embodiments, each R and $R_1$ independently comprises a $C_1$-$C_{14}$ hydrocarbon group or a hydrogen.

In some embodiments, the alkoxylated amino aldehyde adduct comprises a structure selected from the group consisting of

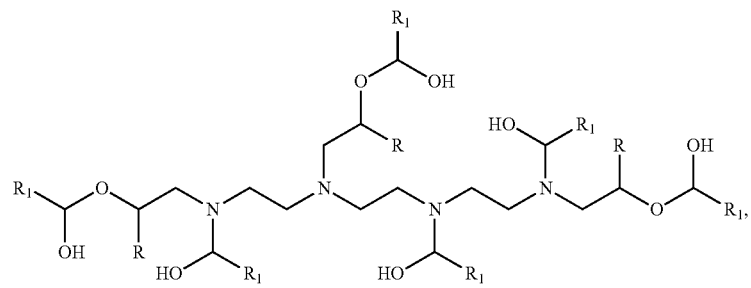

and

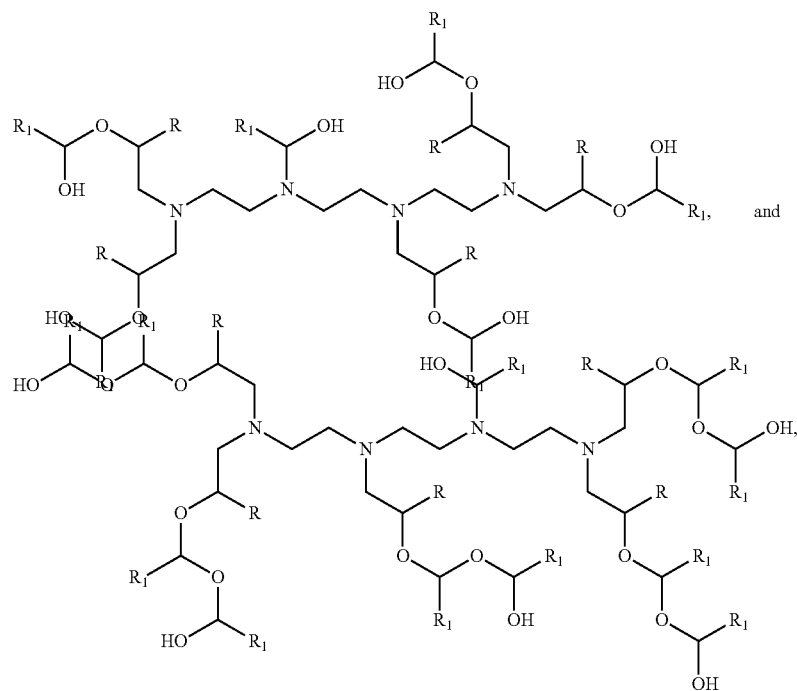

wherein each R is independently selected from a hydrogen, methyl, ethyl, propyl, and/or $CH_2OR_{10}$, where $R_{10}$=H, methyl, ethyl, propyl, isopropyl, butyl, phenyl, benzyl; and wherein each $R_1$ is independently selected from a hydrogen or methyl.

In some embodiments, each R and $R_1$ independently comprise a $C_1$-$C_{14}$ hydrocarbon group or a hydrogen.

In some embodiments, the alkoxylated amino aldehyde adduct comprises a structure selected from the group consisting of

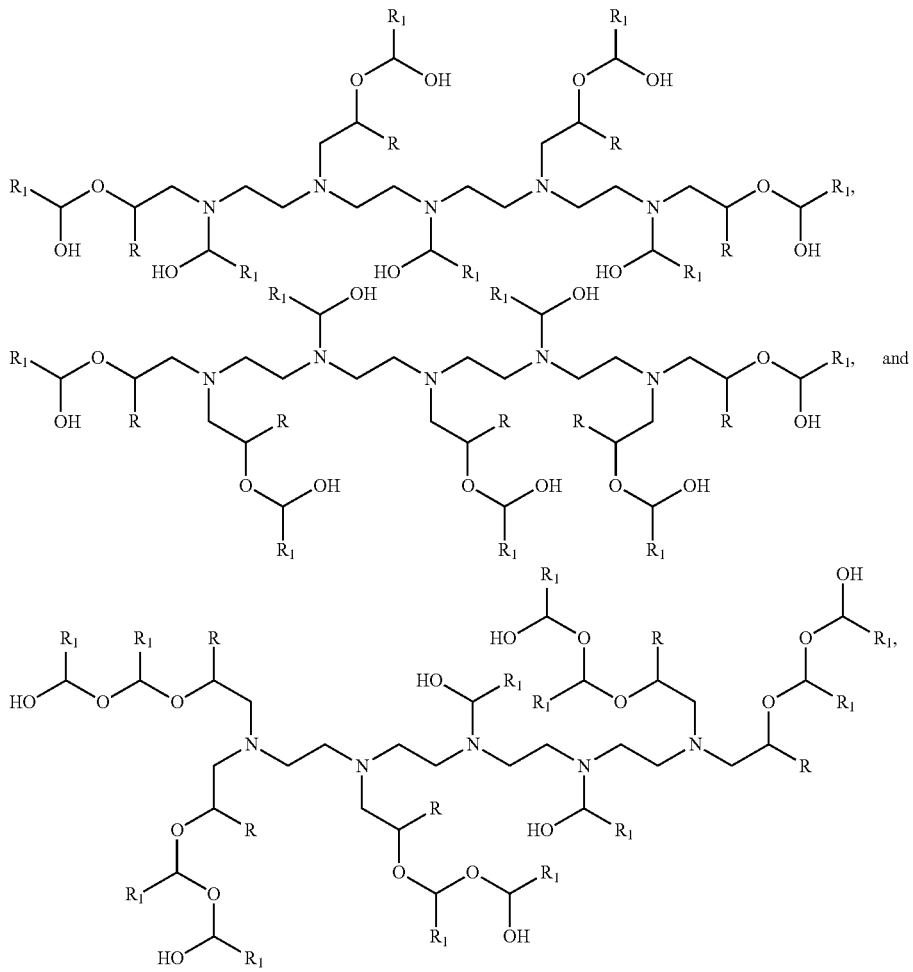

wherein each R is independently selected from a hydrogen, methyl, ethyl, propyl, and/or $CH_2OR_{10}$, where $R_{10}$=H, methyl, ethyl, propyl, isopropyl, butyl, phenyl, benzyl; and wherein each $R_1$ is independently selected from a hydrogen or methyl.

In some embodiments, each R and $R_1$ independently comprises a $C_1$-$C_{14}$ hydrocarbon group or a hydrogen.

In some embodiments, the stream is aqueous, gaseous, organic, or any combination thereof.

In some embodiments, the composition is anhydrous.

In some embodiments, the composition comprises an aqueous solvent or an organic solvent.

The present disclosure also provides scavengers, and, in some embodiments, the scavengers are produced according to the following synthetic scheme:

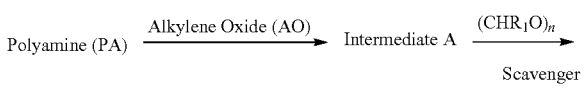

wherein $(CHR_1O)_n$ is formaldehyde when $R_1$=H, and alkylene oxide is ethylene oxide, propylene oxide, butylene oxide, or glycidyl ether.

In some embodiments, the polyamine is selected from the group consisting of a diamine, a triamine, a tetramine, and a pentamine.

Additionally, the present disclosure provides compositions comprising at least one hydrogen sulfide scavenger. In some embodiments, the scavenger comprises a structure selected from the group consisting of:

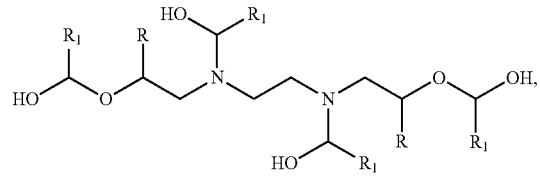
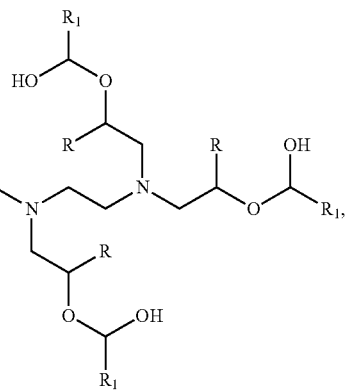
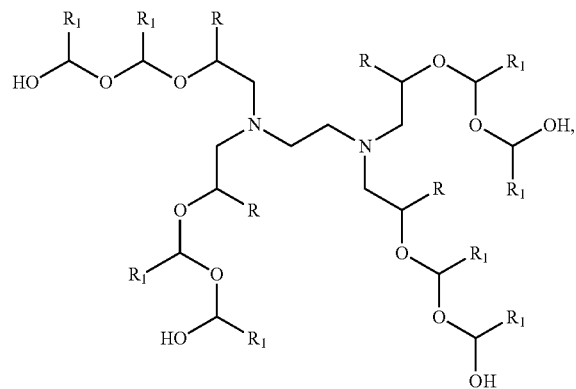
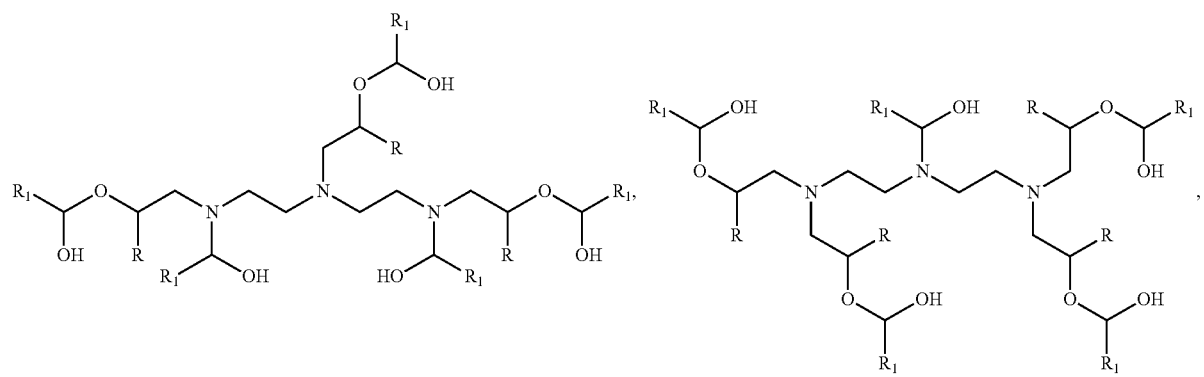
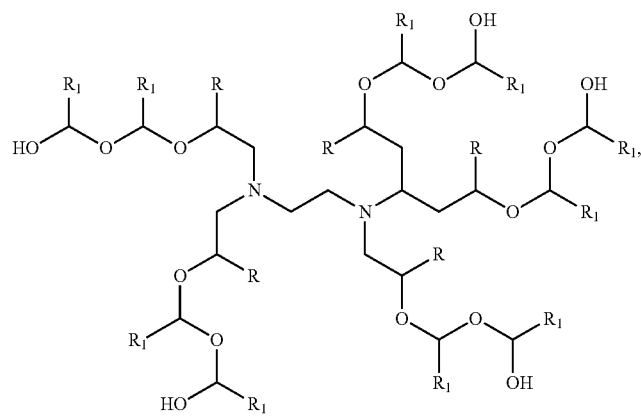

-continued
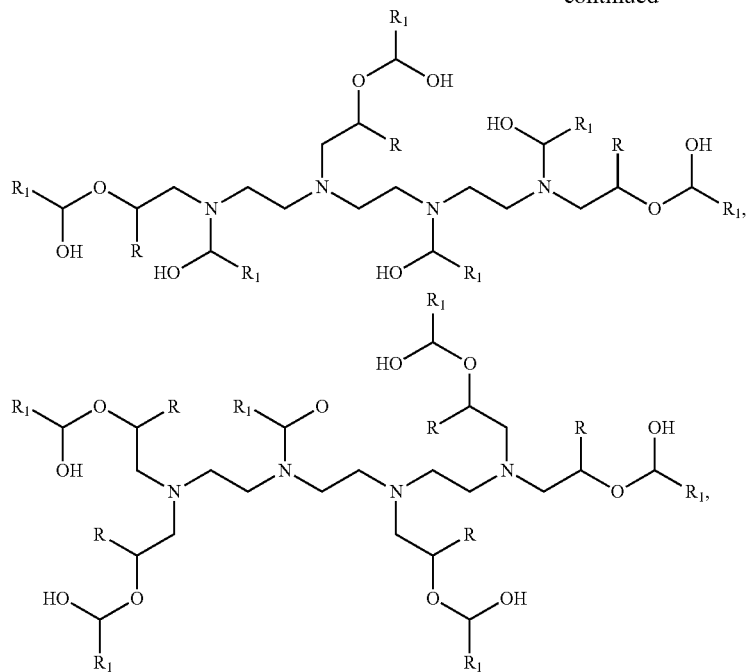
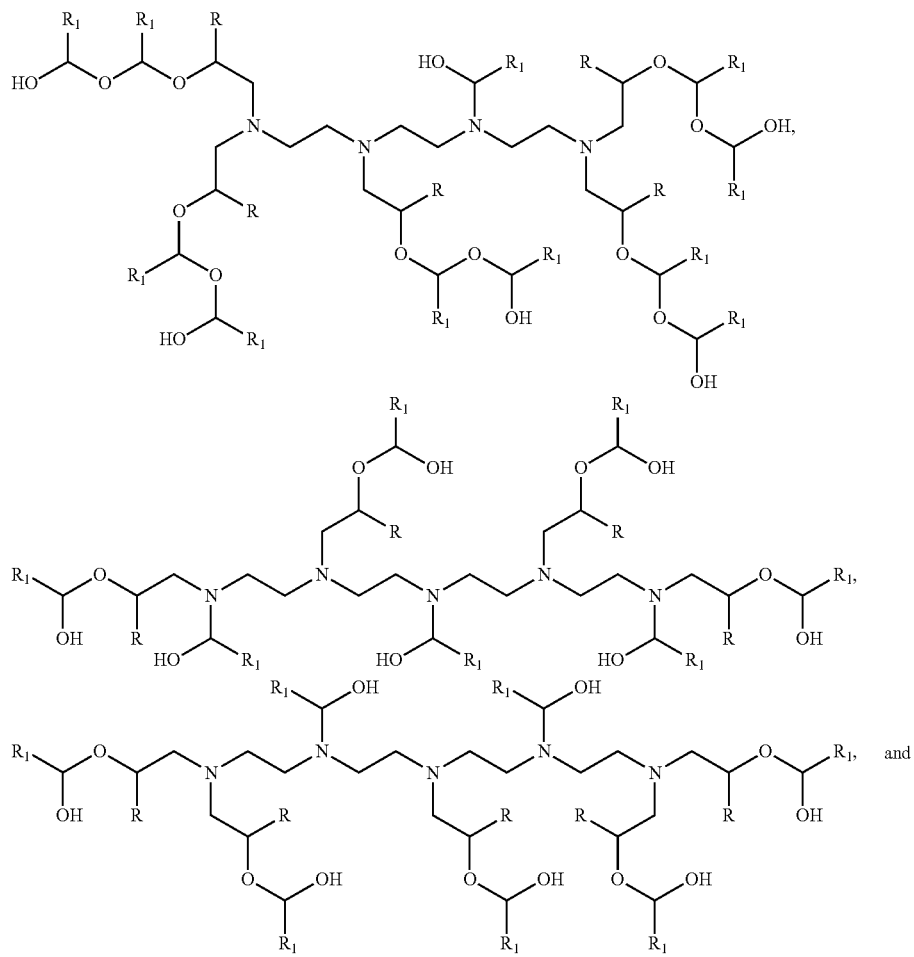

-continued

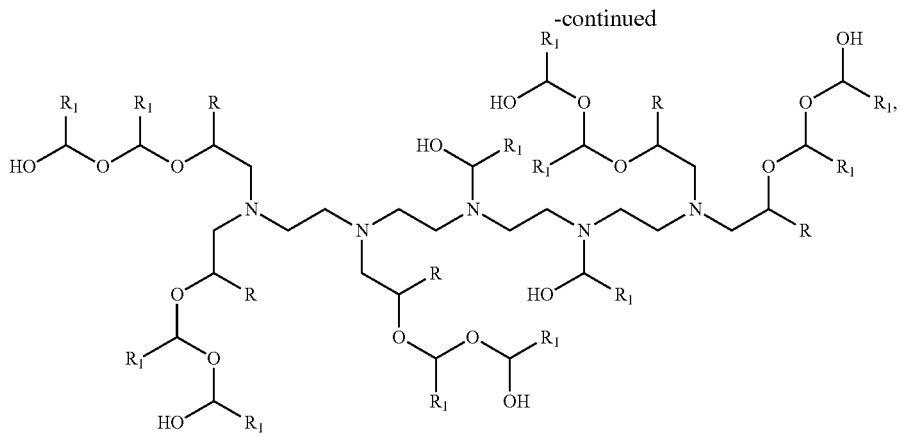

wherein each R is independently selected from a hydrogen, methyl, ethyl, propyl, and/or $CH_2OR_{10}$, where $R_{10}$=H, methyl, ethyl, propyl, isopropyl, butyl, phenyl, benzyl; and wherein each $R_1$ is independently selected from a hydrogen or methyl.

The foregoing Brief Summary provides a broad outline of the features and technical advantages of the present disclosure and allows a better understanding of the detailed disclosure. Additional features and advantages of the disclosure that form the subject of the claims of this application will be described hereinafter. It will be appreciated by those of skill in the art that the conception and specific embodiments disclosed herein may be readily modified, and that other embodiments may exist for carrying out the purposes of the present disclosure without departing from the spirit and scope of the disclosure as set forth in the appended claims.

DETAILED DESCRIPTION

Figure 1:
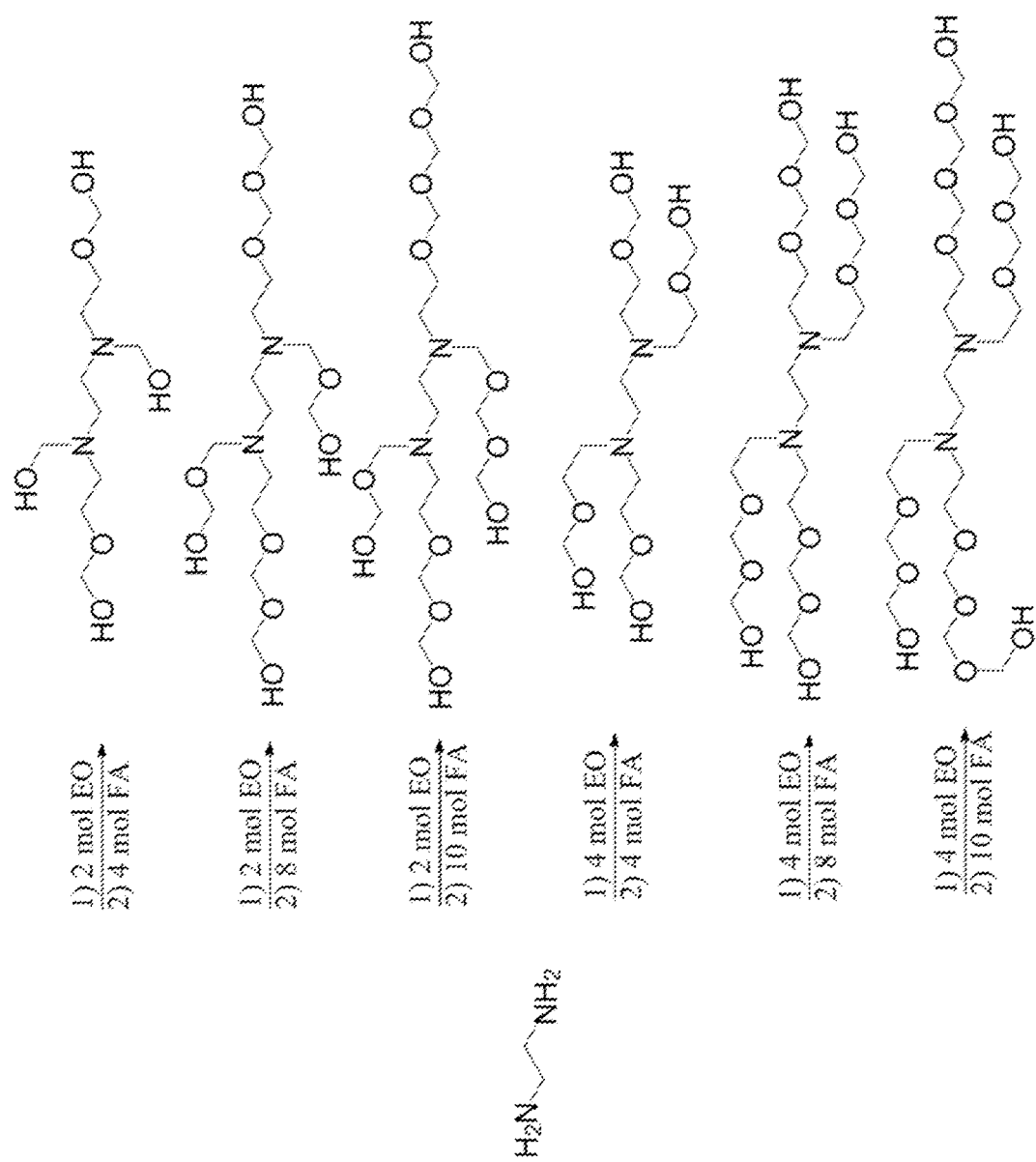
FIG. 1 illustrates the reaction of ethylene diamine (EDA)+ethylene oxide (EO) to form hydrogen sulfide scavengers precursors, followed by reaction with formaldehyde/paraformaldehyde to form scavengers, according to certain embodiments herein.

Various embodiments are described below. The function and relationship of the various elements of the embodiments disclosed herein may be better understood by reference to the following detailed description. However, the invention is not limited to the embodiments explicitly described below. In certain instances, details may have been omitted that are not necessary for an understanding of specific embodiments disclosed herein, such as conventional fabrication and assembly already known to those of skill in the art.

The present disclosure provides compositions and methods that are useful in removing, lowering, sequestering, or otherwise controlling hydrogen sulfide and mercaptans (i.e., thiols). These compositions and methods can be used in any industry where hydrogen sulfide accumulation poses problems, such as industries dealing with crude oil-based, natural gas-based, and/or coal-based products. The present disclosure provides compositions and methods that can reduce or eliminate hydrogen sulfide. Hereinafter, it is understood that the term "treating" in connection with the phrase, for example, "treating hydrogen sulfide" is to be construed as meaning removing, lowering, sequestering, and/or eliminating hydrogen sulfide.

For example, in one aspect, a method of treating hydrogen sulfide may encompass completely eliminating hydrogen sulfide from a hydrocarbon stream. In another aspect, a method of treating hydrogen sulfide may encompass lowering the hydrogen sulfide content in a hydrocarbon stream. In still another aspect, a method of treating hydrogen sulfide may encompass sequestering the hydrogen sulfide content in a hydrocarbon stream, such that some or all of the hydrogen sulfide is no longer available for undesirable reactions or deposition.

As used herein, the term "sequester" or "sequestration" of hydrogen sulfide shall mean and refer to forming a chelate or other stable compound with hydrogen sulfide such that the hydrogen sulfide is no longer available to participate in chemical reactions or is otherwise inactivated, even if the hydrogen sulfide itself is substantially chemically unchanged.

In some embodiments, the present disclosure relates to chemical compositions that are capable of treating hydrogen sulfide. Such compositions comprise compounds that may be generally referred to as scavengers. The disclosed scavengers can effectively treat hydrogen sulfide in water and/or oil mediums, such as water streams or oil streams, in any environment. In some embodiments, the scavengers are anhydrous. The anhydrous scavengers may be blended with non-aqueous solvents, such as hydrocarbon solvents, to produce a composition that can be used in any environment or climate. The anhydrous compositions can optionally be blended with hydrophilic solvents (e.g., alcohols, glycol, polyols) for non-aqueous applications. Alternatively, the compositions may be blended with an aqueous phase for direct use in aqueous applications. In some embodiments, the scavengers may be oil soluble.

In some embodiments, the compositions comprise scavenger compounds comprising one or more alkoxylated polyamino aldehyde or formaldehyde adducts.

For example, in particular embodiments, the scavengers have the following generic formula:

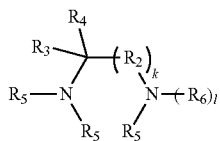

Formula I k=1-3, not=0
l=0-3
provided that when l=0 $R_6=R_5$
provided that each N has at most one H

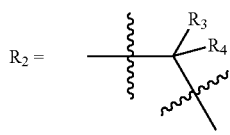

$R_3$=H, methyl, ethyl
$R_4$=H, methyl, ethyl
$R_5$=optionally H, $R_7$, or

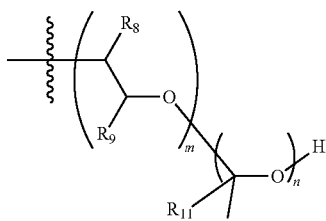

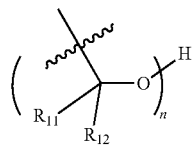

m=0-4
provided that when m=0, $R_5$=H or $R_7$
n=0-4
provided that when n=0, the sum of n in formula>0

$R_8$=H, methyl, ethyl, propyl
$R_9$=H, methyl, ethyl, propyl, $CH_2OR_{10}$
$R_{10}$=H, methyl, ethyl, propyl, isopropyl, butyl, phenyl, benzyl
$R_{11}$=H, methyl, ethyl
$R_{12}$=H, methyl, ethyl

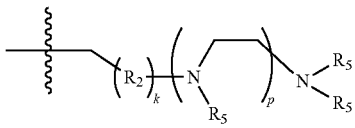

p=0-2
provided that l=0, 1 in Formula I

In some embodiments, the stream is aqueous, gaseous, organic, or any combination thereof. In some embodiments, the composition is anhydrous.

In one aspect, methods are provided for treating hydrogen sulfide in a stream, including adding an effective amount of a composition to the stream, wherein the composition comprises a scavenger, the scavenger comprising an alkoxylated polyamino formaldehyde adduct, wherein the adduct does not comprise a triazine, and reacting the hydrogen sulfide with the scavenger.

In one aspect, a scavenger is provided, wherein the scavenger is produced according to the following synthetic scheme

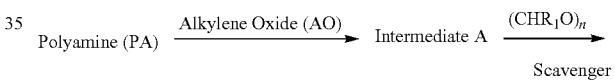

wherein $(CHR_1O)_n$ is formaldehyde when $R_1$=H, and alkylene oxide is ethylene oxide, propylene oxide, butylene oxide, or glycidyl ether.

In some embodiments, the polyamine is selected from a diamine, a triamine, tetramine, and a pentamine.

In one aspect, a composition comprising at least one hydrogen sulfide scavenger is disclosed.

Generally speaking, the presently disclosed scavengers may be prepared by reacting a polyamine (PA) (e.g., diamine, triamine, tetramine, pentamine, etc.) with an alkylene oxide (AO) (e.g., ethylene oxide, propylene oxide, etc.) to form an intermediate, then reacting the intermediate with an aldehyde or formaldehyde source (e.g., formaldehyde, paraformaldehyde) or an alkyl aldehyde (e.g. acetaldehyde) to generate the scavenger product, according to the following reaction scheme:

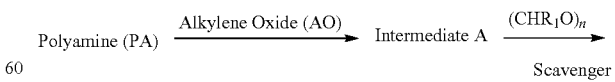

In certain embodiments, intermediate A comprises a secondary or tertiary amine, and does not comprise a primary amine.

For example, scavengers may be synthesized from EDA according to the following synthetic scheme:

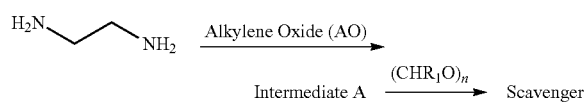

wherein $(CHR_1O)_n$ is a formaldehyde when $R_1=H$, AO=alkylene oxide chosen from EO (ethylene oxide), PO (propylene oxide), and BO (butylene oxide).

A diamine may be reacted with ethylene oxide, propylene oxide, butylene oxide, or any combination of ethylene oxide, propylene oxide, and butylene oxide. The product is then reacted with, for example, formaldehyde, acetaldehyde, etc., to form the scavenger. Illustrative, non-limiting examples of scavengers formed by this reaction include:

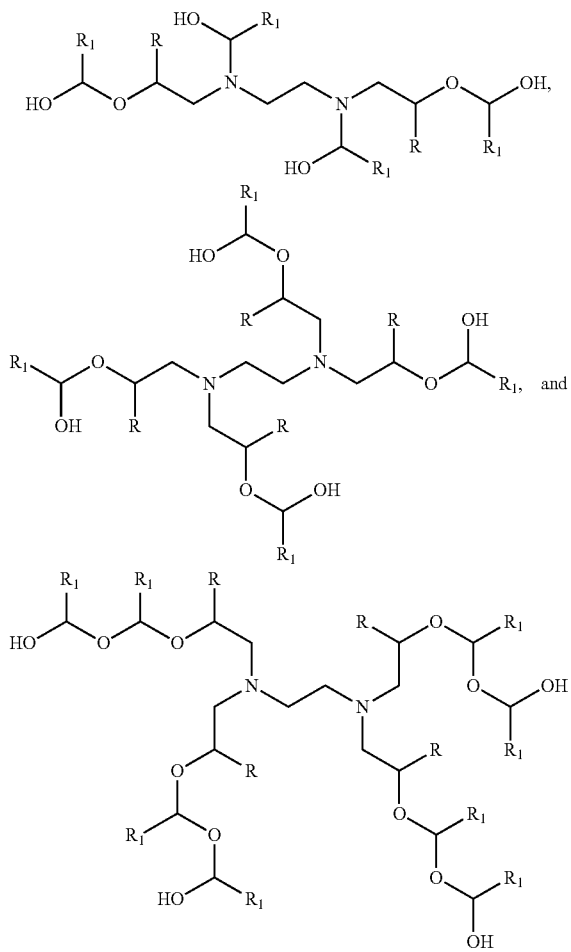

wherein each R is independently selected from a hydrogen, methyl, ethyl, propyl, and/or glycidyl ether $(R_9=CH_2OR_{10})$, where $R_{10}=H$, methyl, ethyl, propyl, isopropyl, butyl, phenyl, benzyl; and wherein each $R_1$ is independently selected from a hydrogen or methyl. The hydrocarbon may be branched or unbranched, saturated or unsaturated. For example, each R and $R_1$ may comprise a $C_1$-$C_{14}$ hydrocarbon group. In certain embodiments, each R and $R_1$ may be independently selected from hydrogen, $C_1$, a $C_2$ group, a $C_3$ group, a $C_4$ group, a $C_5$ group, a $C_6$ group, a $C_7$ group, or any combination thereof. For example, each R and $R_1$ may be independently selected from hydrogen, methyl, ethyl, propyl, butyl, pentyl, hexyl, and/or heptyl groups.

Although the foregoing synthetic scheme depicts a diamine reactant, any polyamine, such as triamine, tetramine, pentamine, etc., may be used to create a scavenger in accordance with the present disclosure. For example, DETA shown below may be reacted with an AO (e.g. EO, PO, and/or BO):

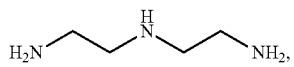

according to the following reaction scheme:

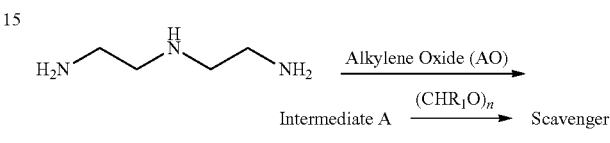

If a triamine is used as the reactant instead of the diamine, products formed that can be used as scavengers include:

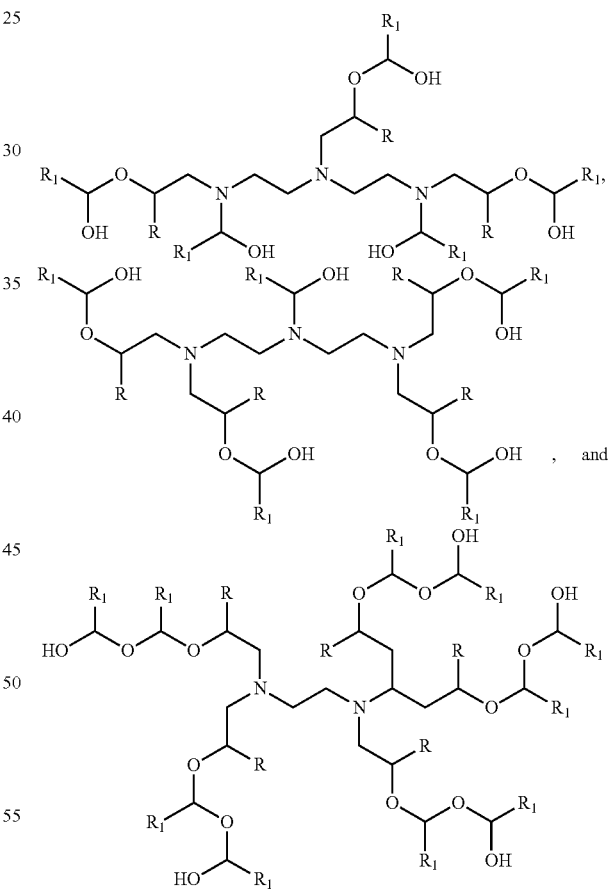

wherein each R is independently selected from a hydrogen, methyl, ethyl, propyl, and/or glycidyl ether $(R_9=CH_2OR_{10})$, where $R_{10}=H$, methyl, ethyl, propyl, isopropyl, butyl, phenyl, benzyl; and wherein each $R_1$ is independently selected from a hydrogen or methyl. The hydrocarbon may be branched or unbranched, saturated or unsaturated. For example, each R and $R_1$ may comprise a $C_1$-$C_{14}$ hydrocarbon group. In certain embodiments, each R and $R_1$ may be independently selected from a hydrogen, $C_1$, a $C_2$ group, a $C_3$ group, a $C_4$ group, a $C_5$ group, a $C_6$ group, a $C_7$ group, or any combination thereof. For example, each R and $R_1$ may be independently selected from methyl, ethyl, propyl, butyl, pentyl, hexyl, and/or heptyl groups.

In other embodiments, a tetramine may be used to react with an AO (e.g. EO, PO, and/or BO).

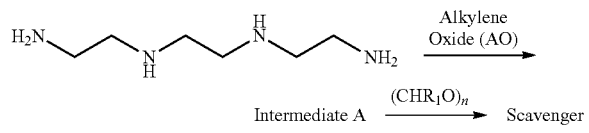

If a tetramine such as triethylene tetramine (TETA) is used as the reactant instead of the diamine, products formed that can be used as scavengers include:

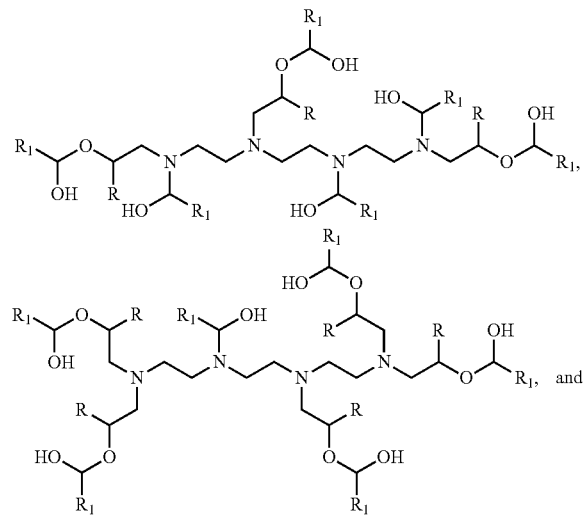

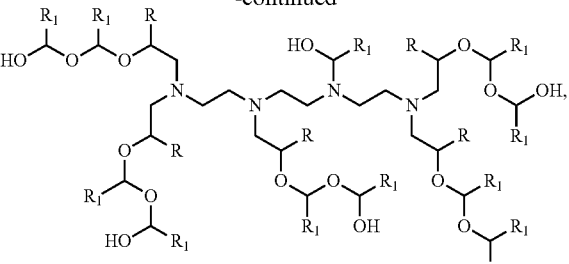

wherein each R is independently selected from a hydrogen, methyl, ethyl, propyl, and/or glycidyl ether ($R_9$=$CH_2OR_{10}$), where $R_{10}$=H, methyl, ethyl, propyl, isopropyl, butyl, phenyl, benzyl; and wherein each $R_1$ is independently selected from a hydrogen or methyl. The hydrocarbon may be branched or unbranched, saturated or unsaturated. For example, each R and $R_1$ may comprise a $C_1$-$C_{14}$ hydrocarbon group. In certain embodiments, each R and $R_1$ may be independently selected from hydrogen, a $C_1$, a $C_2$ group, a $C_3$ group, a $C_4$ group, a $C_5$ group, a $C_6$ group, a $C_7$ group, or any combination thereof. For example, each R and $R_1$ may be independently selected from methyl, ethyl, propyl, butyl, pentyl, hexyl, and/or heptyl groups.

In still further embodiments, a pentamine, such as tetraethylpentatmine (TEPA) may be used to react with AO (e.g. EO, PO, and/or BO):

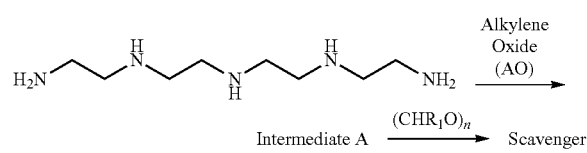

If a pentamine is used as the reactant instead of the diamine, products formed that can be used as scavengers include:

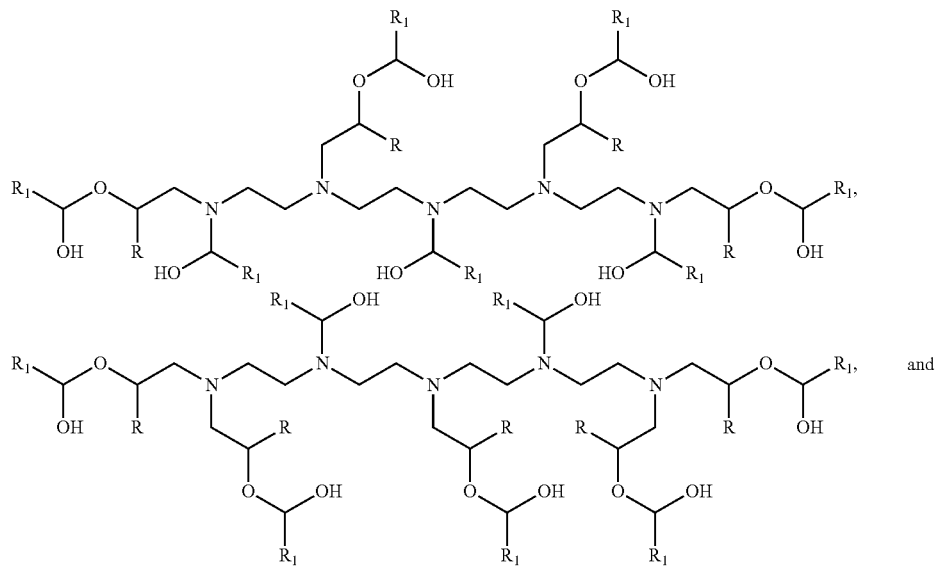

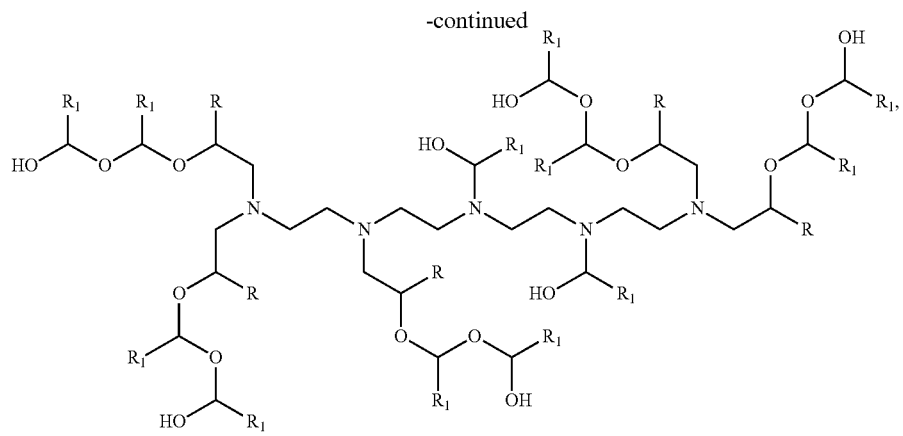

wherein each R is independently selected from a hydrogen, methyl, ethyl, propyl, and/or glycidyl ether ($R_9=CH_2OR_{10}$), where $R_{10}=H$, methyl, ethyl, propyl, isopropyl, butyl, phenyl, benzyl; and wherein each $R_1$ is independently selected from a hydrogen or methyl. The hydrocarbon may be branched or unbranched, saturated or unsaturated. For example, each R and $R_1$ may comprise a $C_1$-$C_{14}$ hydrocarbon group. In certain embodiments, each R and $R_1$ may be independently selected from a hydrogen, $C_1$, a $C_2$ group, a $C_3$ group, a $C_4$ group, a $C_5$ group, a $C_6$ group, a $C_7$ group, or any combination thereof. For example, each R and $R_1$ may be independently selected from methyl, ethyl, propyl, butyl, pentyl, hexyl, and/or heptyl groups.

In addition, branched-chain polyamines may be used as the starting material to react with AO (e.g. EO, PO), and/or BO) to form a branched chain scavenger. For example, either of the branched tetramines or pentamines shown below may be used:

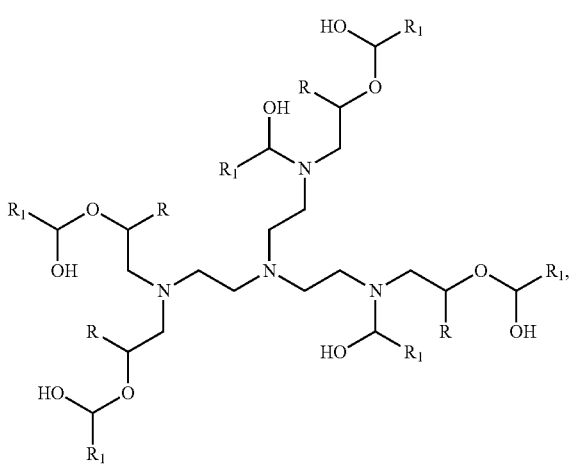

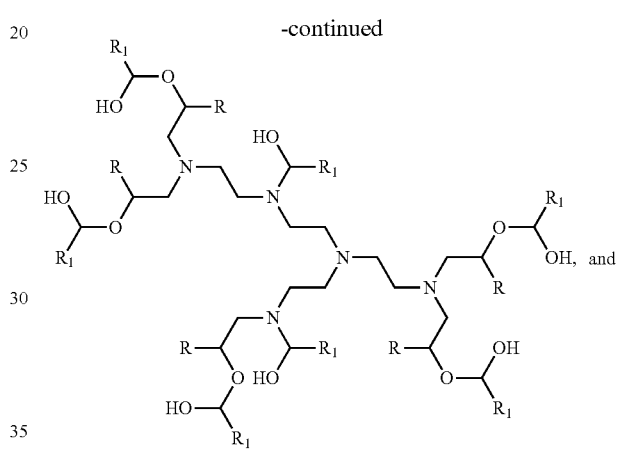

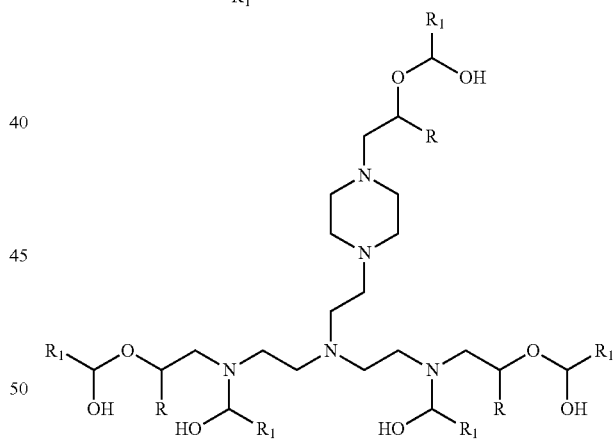

wherein each R is independently selected from a hydrogen, methyl, ethyl, propyl, and/or glcidyl ether ($R_9=CH_2OR_{10}$), where $R_{10}=H$, methyl, ethyl, propyl, isopropyl, butyl, phenyl, benzyl; and wherein each $R_1$ is independently selected from a hydrogen or methyl.

In a reaction of a polyamine with an alkylene oxide, as described herein, the maximum number of oxides (e.g., alkoxy or alcohol groups) that is expected on the scavenger product can be expressed according to the following formula:

Oxides(max)=2+(# of amines in starting polyamine)

For example, in the reaction of EDA with EO, the maximum number of oxides groups that could be present in the scavenger product, depending on stoichiometry and other reaction factors, is four. In no event, however, should the intermediate formed contain a primary amine group, which can lead to undesirable byproducts such as triazines.

While diamine, triamine, tetramine, and pentamine have been illustrated as specific examples, the presently-disclosed scavengers are not limited to production using these specific amines and any polyamine may be used to synthesize the presently-disclosed scavengers. In addition, while many of these specifically-disclosed scavenger embodiments include an ethylene (i.e, two-carbon) bridge between amine groups, it is understood that this bridge may be longer, for example, a propylene or butylene bridge, as provided by Formula I herein, where k=2 or 3.

In some embodiments, the presently disclosed scavengers may also be prepared by reacting a PA with a GE (rather than an alkylene oxide) to form an intermediate, then reacting the intermediate with a formaldehyde source (e.g., formaldehyde, paraformaldehyde), or an alkyl aldehyde (e.g. acetaldehyde) to generate the scavenger product, according to the following reaction scheme:

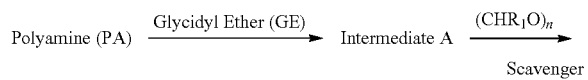

Examples of glycidyl ethers suitable for the above-described reaction include, but are not limited to methyl, ethyl, propyl, iso-propyl, butyl, iso-butyl, tert-butyl, benzyl, phenyl, allyl, bis-phenol, furfuryl, and glyceryl mono and poly glycidyl ethers.

For example, if EDA is reacted with glycidyl ether, products formed that can be used as scavengers include:

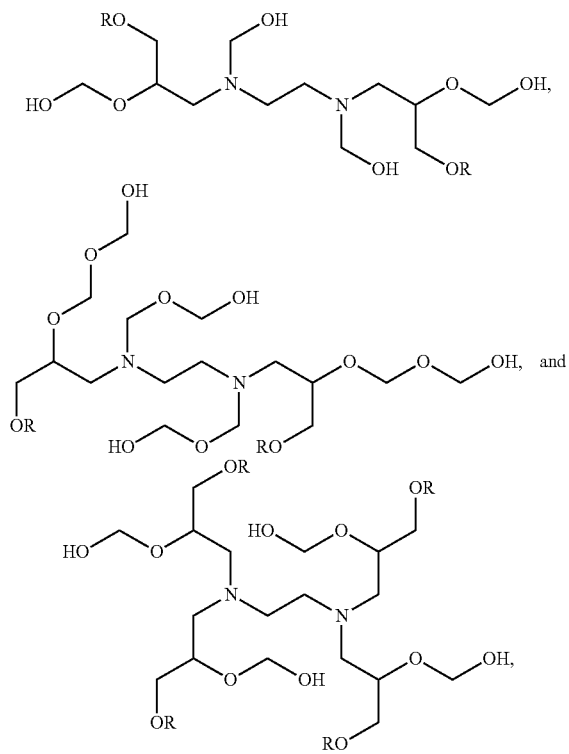

wherein each R is independently selected from a hydrogen, methyl, ethyl, propyl, and/or glycidyl ether ($R_9=CH_2OR_{10}$), where $R_{10}=H$, methyl, ethyl, propyl, iso-propyl, butyl, phenyl, benzyl.

In some embodiments, the amine may be reacted with about 1 to 4 moles of EO, PO, BO, or any combination thereof. In certain embodiments, the amine may be reacted with a mixture of about 1 to about 4 moles of EO/PO. The EO, PO, and/or BO can be present in any ratio in the mixture, provided that the mixture includes about 1 mole to about 4 moles of combined EO, PO, and/or BO with respect to the amine.

The reaction product of the amine and the oxide may then be reacted with about 1 to about 7 moles of formaldehyde, acetaldehyde, propionaldehyde, butaraldehyde, or a combination thereof, to produce stable and reactive hydrogen sulfide scavengers. The formaldehyde can be a solution comprising paraformaldehyde, formalin, or a combination thereof.

Alternatively, the polyamine may be reacted with about 1-4 moles of a glycidyl ether. In certain embodiments, the amine may be reacted with a mixture of about 1 to about 4 moles of GE. The GE can be present in any ratio in the mixture, provided that the mixture includes about 1 mole to about 4 moles of combined GE with respect to the amine.

In some embodiments, the final scavenger product can be made to be water free (e.g. anhydrous) depending upon the intended use of the scavenger.

In one exemplary embodiment, a scavenger may be made by adding about 2 moles of PO to EDA containing 10-25 wt. % isopropanol (IPA) to keep the reactants as a slurry. The resulting mixture may be reacted with about 4 moles of paraformaldehyde, formalin, or a mixture of paraformaldehyde and formalin, and heated to about 70-80° C. to obtain a clear solution. After all paraformaldehyde/formalin goes into solution, the temperature may be raised to distill off the solvent IPA or an IPA/water mixture. After all solvent/water is removed, the product may be cooled to about 80° C. and swept with nitrogen to remove any residual formaldehyde/formalin. In this embodiment, the product was a slightly yellow, viscous liquid that was soluble in both water and propylene carbonate to give a clear solution at 20 wt. % max. aromatic naphtha.

Similarly, in some embodiments, a scavenger according to the present disclosure may be made by reacting EDA with about 4 moles of PO to form a first product, and reacting the first product with 1-4 moles of paraformaldehyde or formalin (or a combination of both). This reaction can be carried out with stirring at about 100° C. until all of the paraformaldehyde/formalin goes into solution. Then, the reaction mixture may be cooled to about 80° C. and swept with nitrogen to remove residual formaldehyde. In this embodiment, the product was a yellow, viscous liquid soluble in propylene carbonate and alcoholic solvents. This product was insoluble in water but produced a hazy solution with an aromatic naphtha solvent. The foregoing procedures may also be used in connection with other starting material reactants, such as a triamine, tetramine, pentamine, EO, BO, or any combination of EO, PO, and BO.

The compositions of the present disclosure may include one or more scavengers as defined herein. The compositions may also optionally include one or more additives. Suitable additives include, but are not limited to, asphaltene inhibitors, paraffin inhibitors, corrosion inhibitors, scale inhibitors, emulsifiers, water clarifiers, dispersants, emulsion breakers, additional hydrogen sulfide scavengers, gas hydrate inhibitors, biocides, pH modifiers, surfactants, solvents, and any combination thereof.

Suitable asphaltene inhibitors include, but are not limited to, aliphatic sulphonic acids; alkyl aryl sulphonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan nionooleate, polyisobutylene succinic anhydride, and any combination thereof.

Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes, and combinations thereof.

Suitable corrosion inhibitors include, but are not limited to, imidazolines, amidoamines, amino esters, quaternary amines, amides, phosphate esters, and any combination thereof.

Suitable scale inhibitors include, but are not limited to, phosphates, phosphate esters, phosphoric acids, phosphonates, phosphonic acids, polyacrylamides, salts of acrylamido-methyl propane sulfonate/acrylic acid copolymer (AMPS/AA), phosphinated maleic copolymer (PHOS/MA), salts of a polymaleic acid/acrylic acid/acrylamido-methyl propane sulfonate terpolymer (PMA/AMPS), and any combination thereof.

Suitable emulsifiers include, but are not limited to, salts of carboxylic acids, products of acylation reactions between carboxylic acids or carboxylic anhydrides and amines, alkyl, acyl and amide derivatives of saccharides (alkyl-saccharide emulsifiers), and any combination thereof.

Suitable water clarifiers include, but are not limited to, inorganic metal salts such as alum, aluminum chloride, and aluminum chlorohydrate, or organic polymers such as acrylic acid based polymers, acrylamide based polymers, polymerized amities, alkanolamines, thiocarbamates, cationic polymers such as diallyldimethylammonium chloride (DADMAC), and any combination thereof.

Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate) and the triamine- and tetramine-polymethylene phosphonates with 2-4 methylene groups between each N atom, at least 2 of the numbers of methylene groups in each phosphonate being different. Other suitable dispersion agents include lignin or derivatives of lignin such as lignosulfonate and naphthalene sulfonic acid and derivatives, and any combination thereof. Suitable dispersants also include dodecyl benzene sulfonate, oxyalkylated alkylphenols, oxyalkylated alkylpnenolic resins, and any combination thereof.

Suitable emulsion breakers include, but are not limited to, dodecylbenzylsulfonic acid (DDBSA), the sodium salt of xylenesulfonic acid (NAXSA), epoxylated and propoxylated compounds, anionic, cationic and nonionic surfactants, resins such as phenolic and epoxide resins, and any combination thereof.

Suitable additional hydrogen sulfide scavengers include, but are not limited to, oxidants (e.g., inorganic peroxides such as sodium peroxide, or chlorine dioxide), aldehydes (e.g., of 1-10 carbons such as formaldehyde or glutaraldehyde or (meth)acrolein), triazines (e.g., monoethanol amine (MEA) triazine, monomethylamine (MMA) triazine, and triazines from multiple amines or mixtures thereof), glyoxal, and any combination thereof.

Suitable gas hydrate inhibitors include, but are not limited to, thermodynamic hydrate inhibitors (THI), kinetic hydrate inhibitors (KHI), anti-agglomerates (AA), and any combination thereof. Suitable thermodynamic hydrate inhibitors include, but are not limited to, NaCl salt, KCl salt, $CaCl_2$ salt, $MgCl_2$ salt, $NaBr_2$ salt, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), alkyl or cyclic esters of alcohols (such as ethyl lactate, butyl lactate, methylethyl benzoate), and any combination thereof. Suitable kinetic hydrate inhibitors and anti-agglomerates include, but are not limited to, polymers and copolymers, polysaccharides (such as hydroxy-ethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, proteins, and any combination thereof.

Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., bronopol and 2-2-dibromo-3-nitrilopropionamide (DBNPA)), sulfur compounds (e.g., isothiazolone, carbamates, and metronidazole), quaternary phosphonium salts (e.g., tetrakis(hydroxymethyl)phosphonium sulfate (THPS)), and combinations thereof. Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, peroxides, and any combination thereof.

Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include NaOH, KOH, Ca(OH)$_2$, CaO, Na$_2$CO$_3$, KHCO$_3$, K$_2$CO$_3$, NaHCO$_3$, MgO, and Mg(OH)$_2$. In addition, suitable pH modifiers include acids such as mineral acids, acetic acid, and acrylic acid.

Suitable surfactants include, but are not limited to, anionic surfactants, cationic surfactants, nonionic surfactants, and combinations thereof. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates, and combinations thereof. Cationic surfactants include alkyl trimethyl quaternary ammonium salts, alkyl dimethyl benzyl quaternary ammonium salts, dialkyl dimethyl quaternary ammonium salts, imidazolinium salts, and combinations thereof. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters, and combinations thereof. Also included are betaines and sultanes, amphoteric surfactants such as alkyl amphoacetates and amphodiacetates, alkyl amphopropripionates and amphodipropionates, alkyliminodiproprionate, and combinations thereof.

In certain embodiments, the surfactant may be a quaternary ammonium compound, an amine oxide, an ionic or non-ionic surfactant, or any combination thereof. Suitable quaternary amine compounds include, but are not limited to, alkyl benzyl ammonium chloride, benzyl cocoalkyl(C$_{12}$-C$_{18}$)dimethylammonium chloride, dicocoalkyl (C$_{12}$-C$_{18}$)dimethylammonium chloride, disallow dimethylammonium chloride, di(hydrogenated tallow alkyl)dimethyl quaternary ammonium methyl chloride, methyl bis(2-hydroxyethyl cocoalkyl(C$_{12}$-C$_{18}$) quaternary ammonium chloride, dimethyl(2-ethyl) tallow ammonium methyl sulfate, n-dodecylbenzyldimethylammonium chloride, n-octadecylbenzyldimethyl ammonium chloride, n-dodecyltrimethylammonium sulfate, soya alkyltrimethylammonium chloride, and hydrogenated tallow alkyl (2-ethylthyexyl) dimethyl quaternary ammonium methyl sulfate.

Suitable solvents include, but are not limited to, water, isopropanol, methanol, ethanol, 2-ethylhexanol, heavy aromatic naphtha, toluene, ethylene glycol, ethylene glycol monobutyl ether (EGMBE), diethylene glycol monoethyl ether, xylene, and combinations thereof. Representative polar solvents suitable for formulation with the composition include water, brine, seawater, alcohols (including straight chain or branched aliphatic such as methanol, ethanol, propanol, isopropanol, butanol, 2-ethylhexanol, hexanol, octanol, decanol, 2-butoxyethanol, etc.), glycols and derivatives (ethylene glycol, 1,2-propylene glycol, 1,3-propylene glycol, ethylene glycol monobutyl ether, etc.), ketones (cyclohexanone, diisobutylketone), N-methylpyrrolidinone (NMP), N,N-dimethylformamide and the like. Representative of non-polar solvents suitable for formulation with the composition include aliphatics such as pentane, hexane, cyclohexane, methylcyclohexane, heptane, decane, dodecane, diesel, and the like; aromatics such as toluene, xylene, heavy aromatic naphtha, fatty acid derivatives (acids, esters, amides), and the like.

In some embodiments, the solvent is a polyhydroxylated solvent, a polyether, an alcohol, or a combination thereof.

In certain embodiments, the solvent is monoethyleneglycol, methanol, dimethyl sulfoxide (DMSO), dimethylformamide (DMF), tetrahydrofuran (THF), or a combination thereof.

In some embodiments, a composition of the present disclosure may comprise one or more scavengers, optionally one or more additives, and from 0 to about 80% by weight of one or more solvents, based on the weight of the composition. In certain embodiments, a composition of the present disclosure may comprise from 0 to about 50% by weight of one or more solvents, based on the weight of the composition. In some embodiments, the composition may comprise from about 20% to about 50% by weight of one or more solvents, based on the weight of the composition.

The presently disclosed compositions comprising one or more hydrogen sulfide scavengers may be used to treat hydrogen sulfide in any industrial application where the treatment of hydrogen sulfide is desirable. For example, when working with crude oil based products, natural gas based products, and/or coal based products, hydrogen sulfide will generally pose certain problems and the presently disclosed scavengers may be used to eliminate or significantly mitigate such problems.

The compositions may be used for sweetening a gas or liquid, such as a sour gas or sour liquid. The compositions may be used for scavenging hydrogen sulfide from an oil or aqueous stream by treating said stream with an effective amount of a composition comrising a scavenger, as described herein. The compositions can be used in any industry where it is desirable to capture hydrogen sulfide. In certain embodiments, the compositions may be used in water systems, condensate/oil systems/gas systems, or any combination thereof. In oil field operations, the compositions may be used in both upstream and downstream applications.

In certain embodiments, the compositions can be applied to a gas or liquid produced or used in the production, transportation, storage, and/or separation of crude oil or natural gas. In certain embodiments, the compositions can be applied to a stream used or produced in a coal-fired process, such as a coal-fired power plant. In certain embodiments, the compositions can be applied to a stream produced or used in a waste-water process, a farm, a slaughter house, a land-fill, a municipality waste-water plant, a mining process, a papermaking process, a coking coal process, or a biofuel process.

The compositions may be added to any stream containing hydrogen sulfide or a stream that may be exposed to hydrogen sulfide. A fluid to which the compositions may be introduced may be an aqueous medium. The aqueous medium may comprise water, gas, and/or liquid hydrocarbon. A fluid to which the compositions are introduced may be a liquid hydrocarbon. The liquid hydrocarbon may be any type of liquid hydrocarbon including, but not limited to, crude oil, heavy oil, processed residual oil, bitminous oil, coker oils, coker gas oils, fluid catalytic cracker feeds, gas oil, naphtha, fluid catalytic cracking slurry, diesel fuel, fuel oil, jet fuel, gasoline, and kerosene.

An aqueous and/or oil-based stream treated with a composition of the present disclosure may be at any selected temperature, such as ambient temperature, a temperature lower than ambient temperature, or a temperature elevated above ambient temperature. In certain embodiments, the stream may be at a temperature of from about 40° C. to about 250° C. In some embodiments, the stream may be at a temperature of from −50° C. to 300° C.

The stream in which the compositions are introduced may be contained in and/or exposed to many different types of apparatuses. For example, the stream may be contained in an apparatus that transports fluid or gas from one point to another, such as an oil and/or gas pipeline. In certain embodiments, the apparatus may be part of an oil and/or gas refinery, such as a pipeline, a separation vessel, a dehydration unit, or a gas line. The stream may be contained in and/or exposed to an apparatus used in oil extraction and/or production, such as a wellhead. The apparatus may be part of a coal-fired power plant. The apparatus may be a scrubber (e.g., a wet flue gas desulfurizer, a spray dry absorber, a dry sorbent injector, a spray tower, a contact or bubble tower, or the like). The apparatus may be a cargo vessel, a storage vessel, a holding tank, or a pipeline connecting the tanks, vessels, or processing units. In certain embodiments, the stream may be contained in water systems, condensate/oil systems/gas systems, or any combination thereof.

The compositions may be introduced into a stream by any appropriate method for ensuring dispersal of the scavenger through the fluid. The compositions may be injected using mechanical equipment such as chemical injection pumps, piping tees, injection fittings, atomizers, quills, and the like. The compositions may be introduced with or without one or more additional polar or non-polar solvents depending upon the application and requirements. In certain embodiments, the compositions may be pumped into an oil and/or gas pipeline using an umbilical line. In some embodiments, capillary injection systems can be used to deliver the compositions to a selected fluid. In particular embodiments, the compositions can be introduced into a liquid and mixed. The compositions can be injected into a stream as an aqueous or nonaqueous solution, mixture, or slurry. In some embodiments, the stream may be passed through an absorption tower comprising a composition as disclosed herein.

The compositions may be applied to an aqueous and/or oil-based stream to provide a scavenger concentration of about 1 parts per million (ppm) to about 1,000,000 ppm, about 1 ppm to about 100,000 ppm, about 10 ppm to about 75,000 ppm, about 100 ppm to about 45,000 ppm, about 500 ppm to about 40,000 ppm, about 1,000 ppm to about 35,000 ppm, about 3,000 ppm to about 30,000 ppm, about 4,000 ppm to about 25,000 ppm, about 5,000 ppm to about 20,000 ppm, about 6,000 ppm to about 15,000 ppm, or about 7,000 ppm to about 10,000 ppm.

Each particular system or application has its own requirements and thus the compositions comprising the scavengers may be applied at any effective dosage that can be selected by one having ordinary skill in the art depending upon the particular application and the relevant factors associated with that application. For example, a stream containing large quantities of hydrogen sulfide may require a higher dose rate. In certain embodiments, the compositions may be applied to a stream in an equimolar amount or greater relative to hydrogen sulfide present in the stream.

The hydrogen sulfide in the stream may be reduced by any amount by treatment with a composition of the present disclosure. The actual amount of residual hydrogen sulfide after treatment may vary depending on the starting amount. In certain embodiments, the hydrogen sulfide may be completely eliminated from the stream or it may be reduced to levels of about 150 ppm by volume or less, as measured in the vapor phase, based on the volume of the liquid media.

In some embodiments, the compositions of the present disclosure may be soluble in an aqueous phase such that the captured sulfur-based species (e.g. hydrogen sulfide) will migrate into the aqueous phase. If an emulsion is present, the captured sulfur-based species can be migrated into the aqueous phase from a hydrocarbon phase (e.g., crude oil) and removed with the aqueous phase. If no emulsion is present, a water wash can be added to attract the captured sulfur-based species. In certain embodiments, the compositions can be added before a hydrocarbon (e.g., crude oil) is treated in a desalter, which emulsifies the hydrocarbon media with a water wash to extract water soluble contaminants and separates and removes the water phase from the hydrocarbon.

Optionally, demulsifiers may be added to aid in separating water from the hydrocarbon. In certain embodiments, the demulsifiers include, but are not limited to, oxyalkylated organic compounds, anionic surfactants, nonionic surfactants or mixtures of these materials. The oxyalkylated organic compounds include, but are not limited to, phenol-formaldehyde resin ethoxylates and alkoxylated polyols. The anionic surfactants include alkyl or aryl sulfonates, such as dodecylbenzenesulfonate. These demulsifiers may be added in amounts to contact the water from about 1 to about 1000 ppm by weight based on the weight of the hydrocarbon.

EXAMPLES

Example 1

1) Propoxylated ethylenediamine (EDA) 118.8 g, 0.50 mole (2 moles of propylene oxide in 20% IPA) was charged into a 500 mL four-neck RB flask fitted with a mechanical stirrer, a condenser attached on top of a Dean Stark trap and a nitrogen inlet attached to an addition funnel and a thermocouple to control the temperature. It was heated to 60-65° C. to make it clear and was charged with paraformaldehyde (66.0 g, 91% active, 2.00 g mole) and heated with stirring until all paraformaldehyde disappeared or reacted. The temperature was slowly raised to 100° C. to distill off IPA from the reaction mixture. The last traces of IPA and free formaldehyde was removed by sweeping with nitrogen 25-30 mL/min for an hour. The reaction mixture is cooled to room temperature and the product was bottled (155.50 g) and about 25.50 g of distillate including IPA and possible water. The yield was quantitative and no formaldehyde deposits in the condenser during nitrogen sweep were observed.

2) Propoxylated ethylenediamine (EDA) 154.00 g, 0.50 mole, soft solid (4 moles of propylene oxide in 10% aromatic naphtha) was charged into a 500 mL four-neck RB flask fitted with a mechanical stirrer, a condenser attached on top of a Dean Stark trap and a nitrogen inlet attached to an addition funnel and a thermocouple to control the temperature. It was heated to 70-75° C. to make it clear and was charged with paraformaldehyde (66.00 g, 91% active, 2.00 g mole) and heated with stirring until all paraformaldehyde disappeared or reacted. The temperature was slowly raised to 100° C. to make a clear reaction product. The last traces of formaldehyde and water were removed by sweeping with nitrogen 25-30 ml/min. for an hour. The reaction mixture was cooled to 60° C. temperature and the product was bottled (210.50 g). The product was clear but viscous and the yield was quantitative and no formaldehyde deposits in the condenser during nitrogen sweep were observed.

FIGS. 1-7 illustrate examples of specific reaction schemes suitable for producing hydrogen sulfide scavengers according to methods disclosed herein, as follows.

FIG. 1 illustrates the reaction of EDA with EO followed by reaction of the intermediate with formaldehyde to form various scavengers.

Figure 2A:
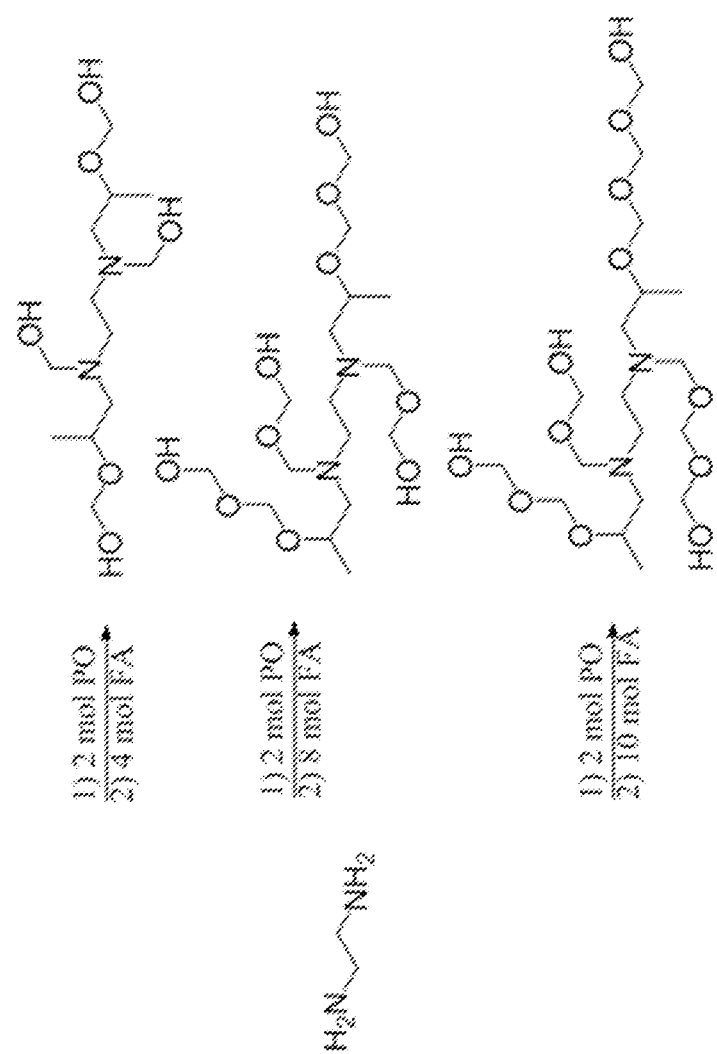
FIGS. 2A and 2B illustrate the reaction of EDA+propylene oxide (PO) to form hydrogen sulfide scavengers precursors, followed by reaction with formaldehyde/paraformaldehyde to form scavengers, according to certain embodiments herein.
Figure 2B:
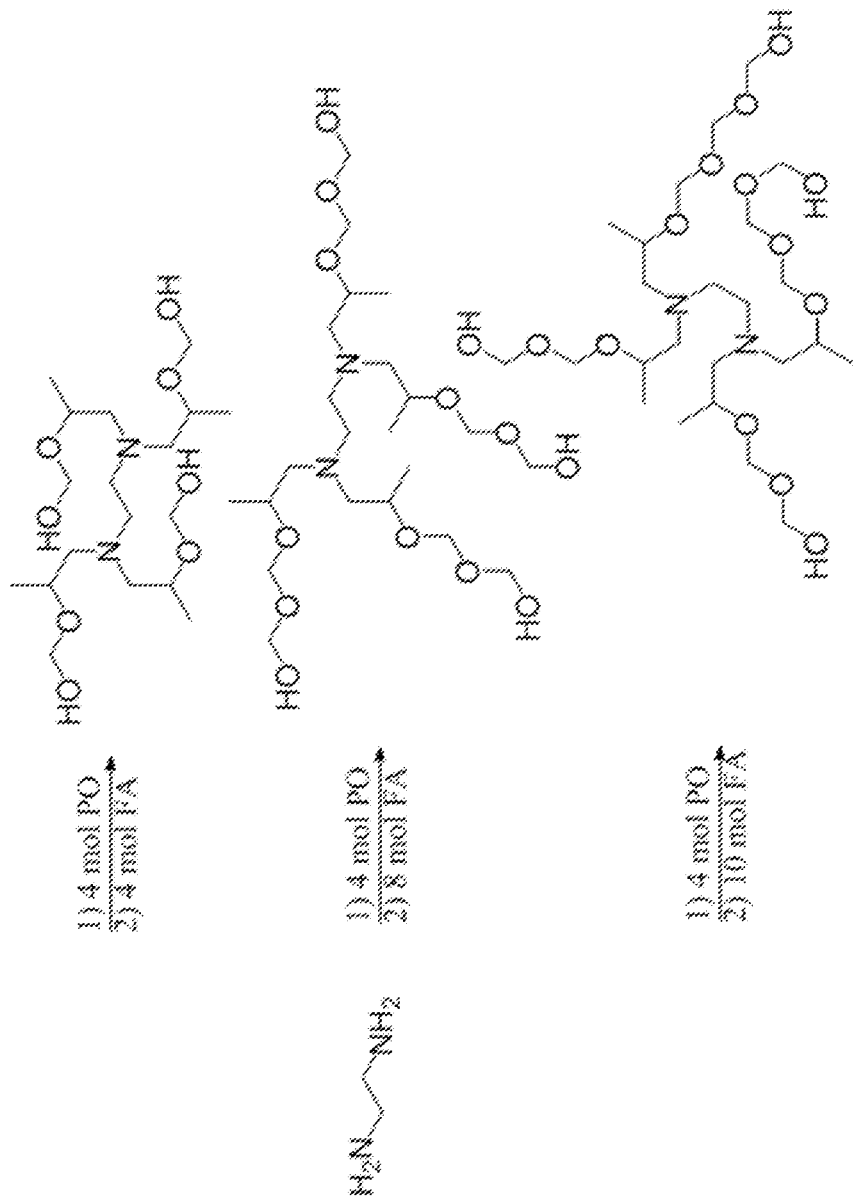

FIGS. 2A and 2B illustrate the reaction of EDA with PO followed by reaction of the intermediate with formaldehyde to form various scavengers.

Figure 3A:
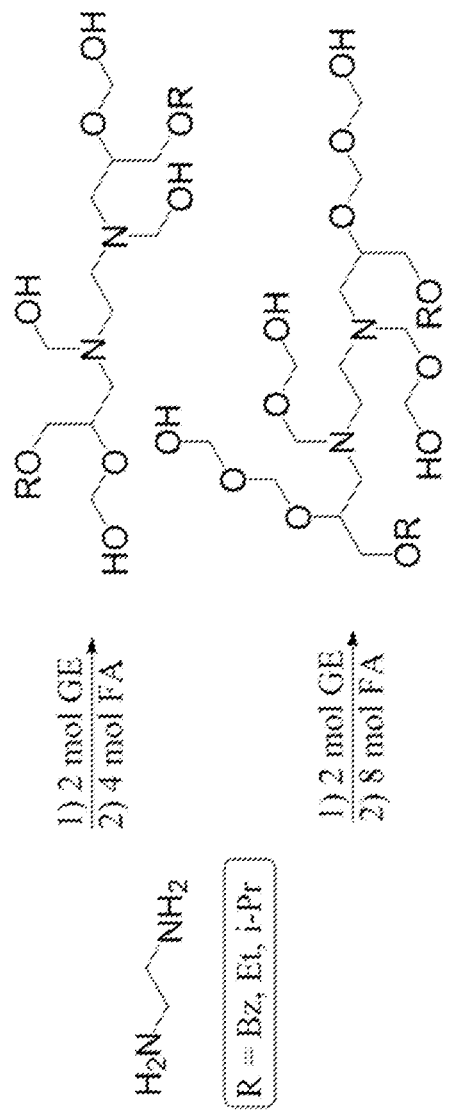
FIGS. 3A and 3B illustrate the reaction of EDA+glycidyl ether (GE) to form hydrogen sulfide scavengers precursors, followed by reaction with formaldehyde/paraformaldehyde to form scavengers, according to certain embodiments herein.
Figure 3B:
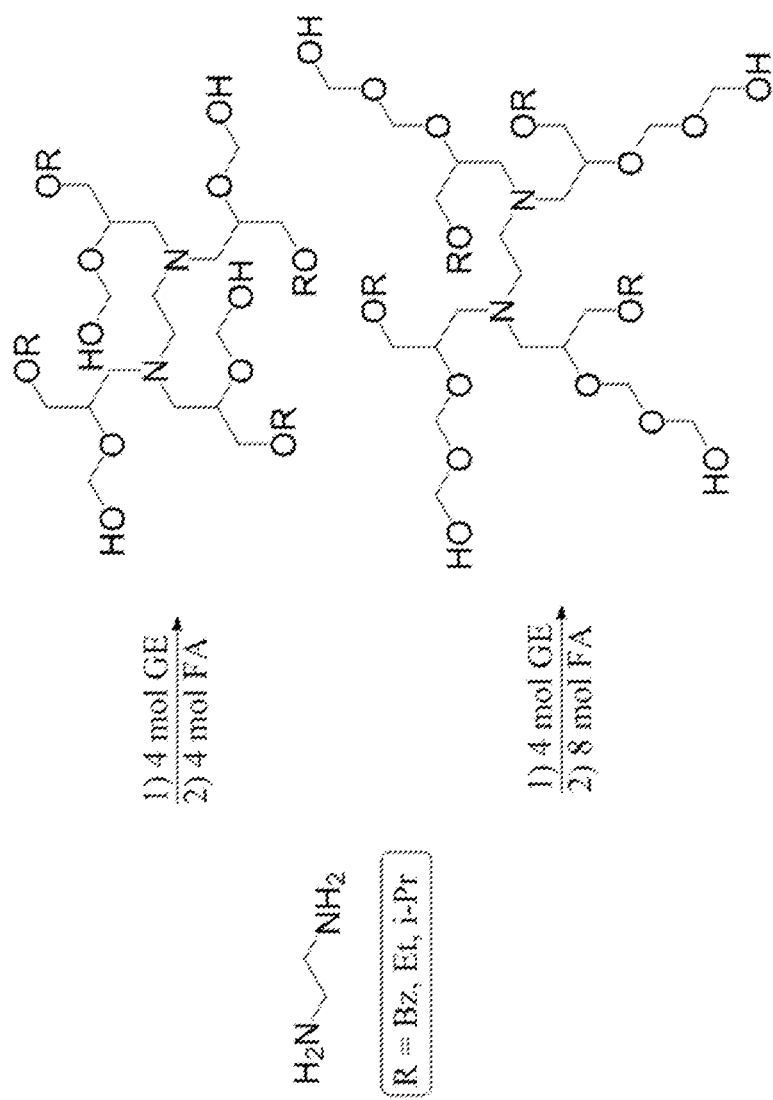

FIGS. 3A and 3B illustrate the reaction of DETA with GE followed by reaction of the intermediate with formaldehyde to form various scavengers.

Figure 4:
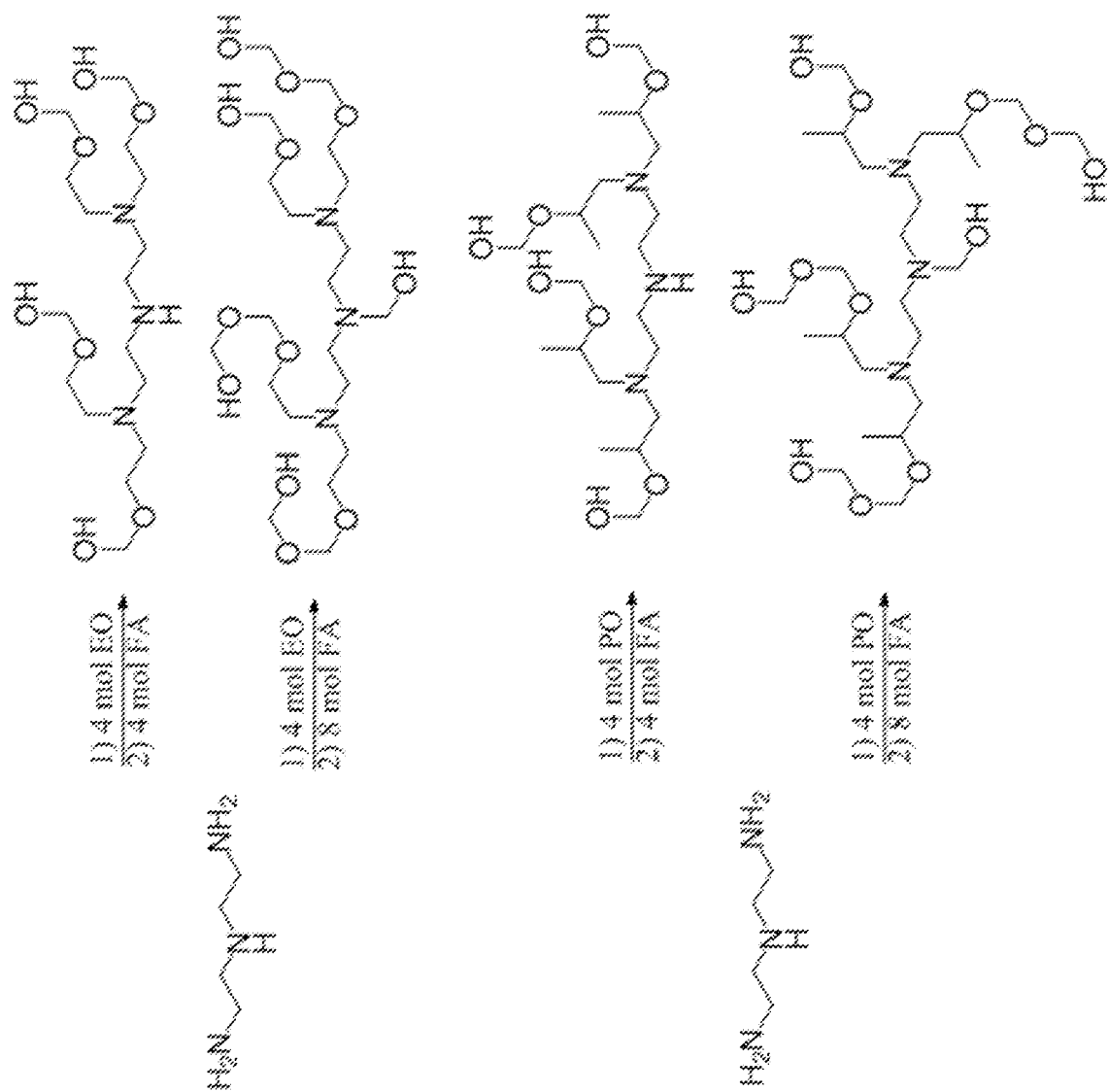
FIG. 4 illustrates the reaction of diethylene triamine (DETA)+EO or PO to form hydrogen sulfide scavenges precursors, followed by reaction with formaldehyde/paraformaldehyde to form scavengers, according to certain embodiments herein.

FIG. 4 illustrates the reaction of DETA with EO or PO followed by reaction of the intermediate with formaldehyde to form various scavengers.

Figure 5:
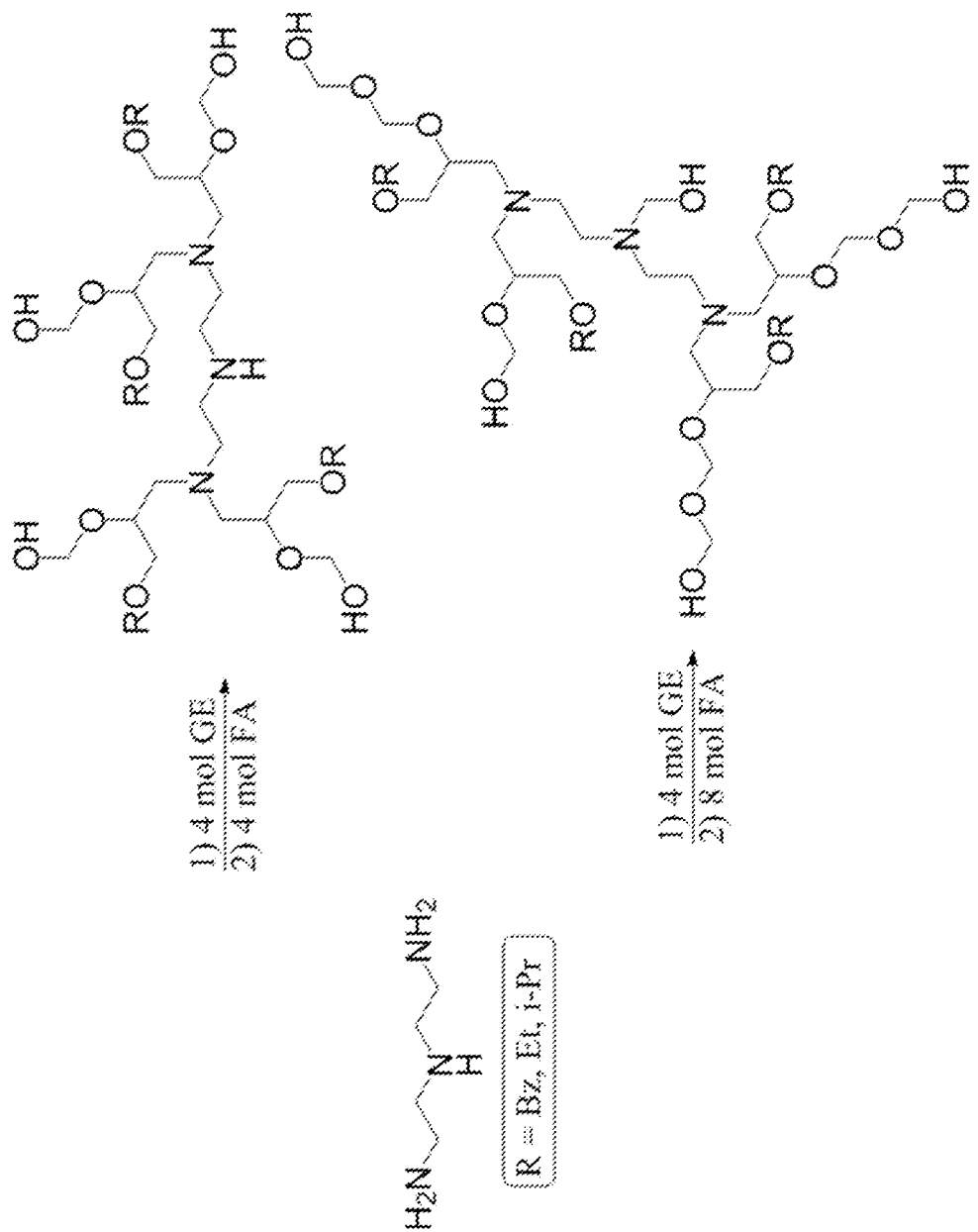
FIG. 5 illustrates the reaction of DETA+GE to form hydrogen sulfide scavengers precursors, followed by reaction with formaldehyde/paraformaldehyde to form scavengers, according to certain embodiments herein.

FIG. 5 illustrates the reaction of DETA with GE followed by reaction of the intermediate with formaldehyde to form various scavengers.

Figure 6A:
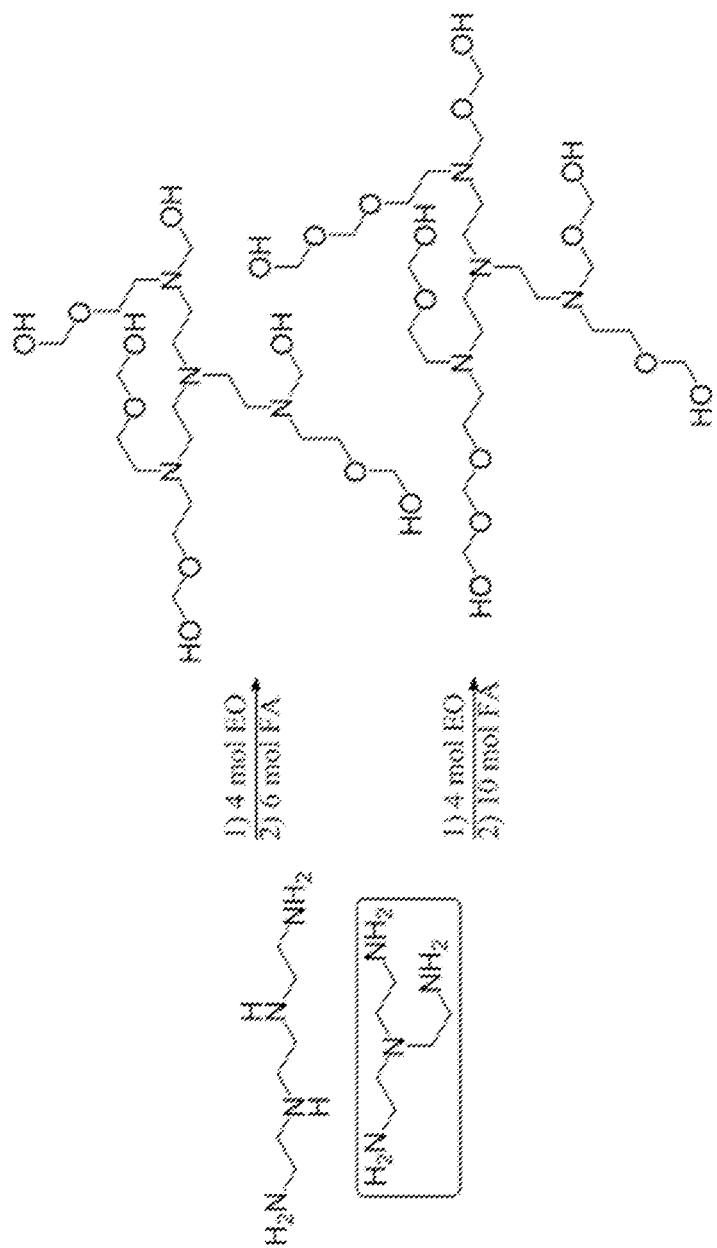
FIGS. 6A and 6B illustrate the reaction of triethylene tetramine (TETA)+EO or PO to form hydrogen sulfide scavengers precursors, followed by reaction with formaldehyde/paraformaldehyde to form scavengers, according to certain embodiments herein.
Figure 6B:
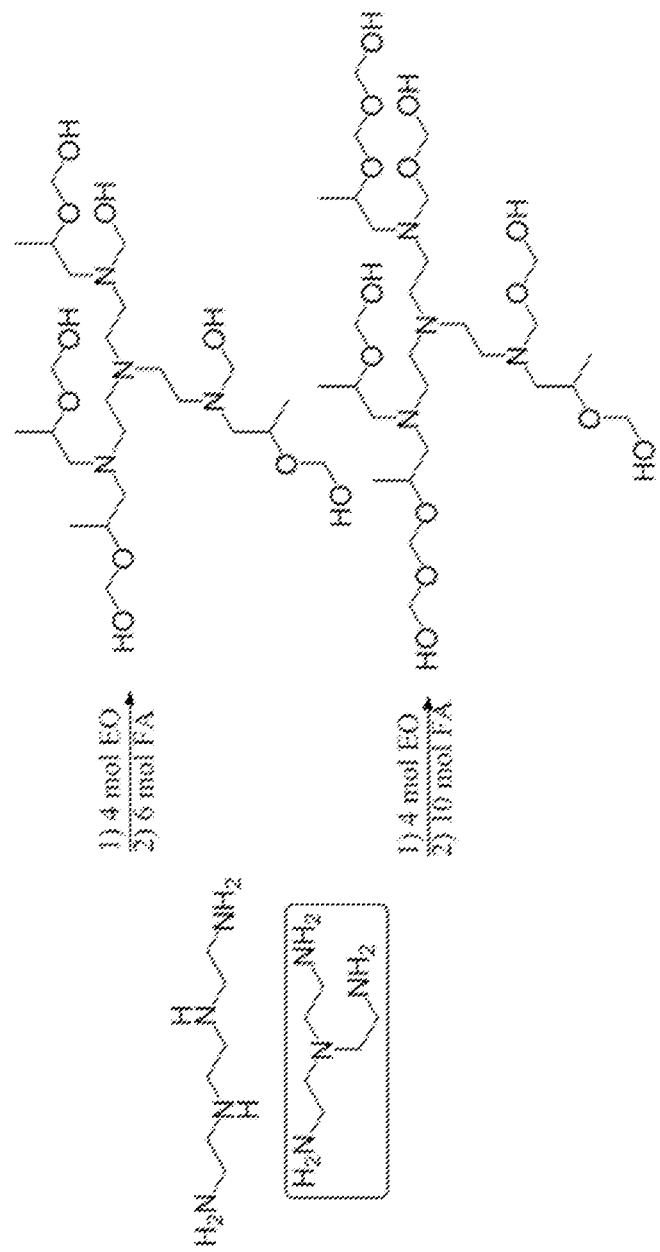

FIGS. 6A and 6B illustrate the reaction of TETA with EO or PO followed by reaction of the intermediate with formaldehyde to form various scavengers.

Figure 7A:
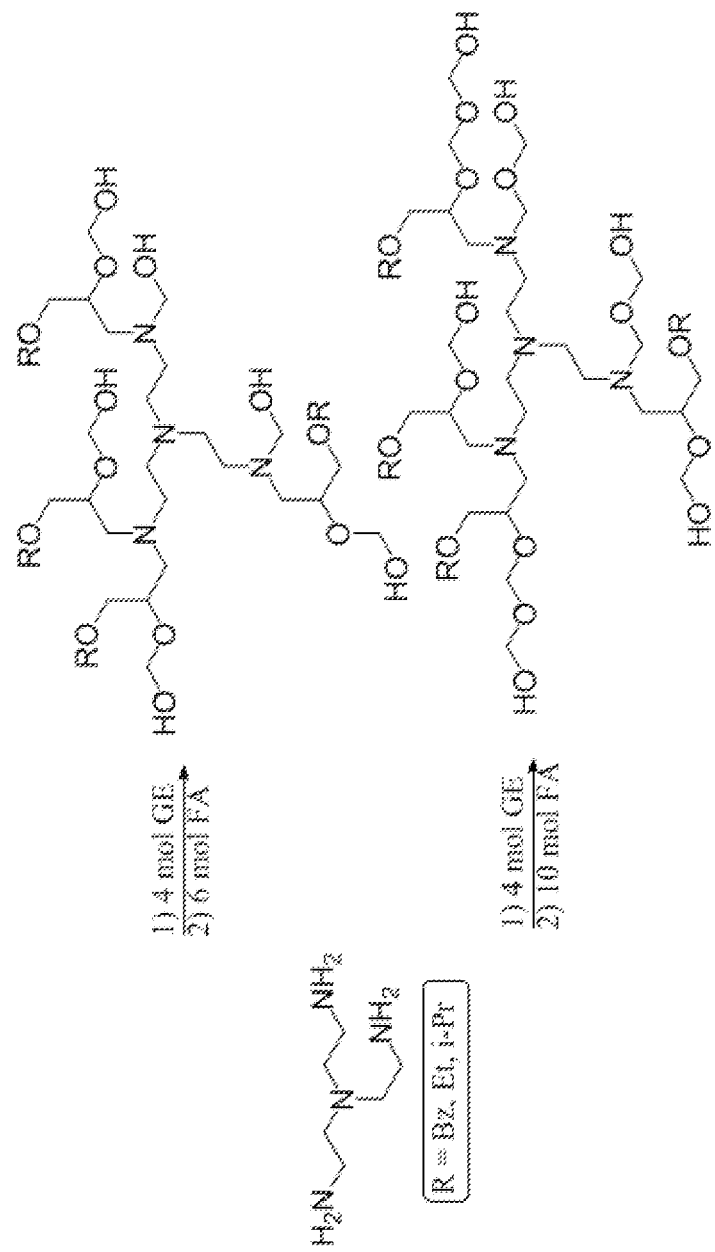
FIGS. 7A, 7B and 7C illustrate the reaction of TETA+GE to form hydrogen sulfide scavenger precursors, followed by reaction with formaldehyde/paraformaldehyde to form scavengers, according to certain embodiments herein.
Figure 7B:
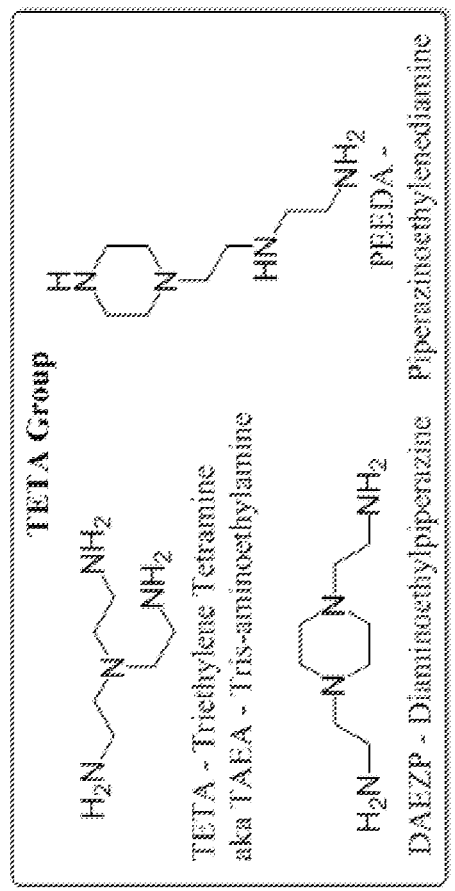
Figure 7C:
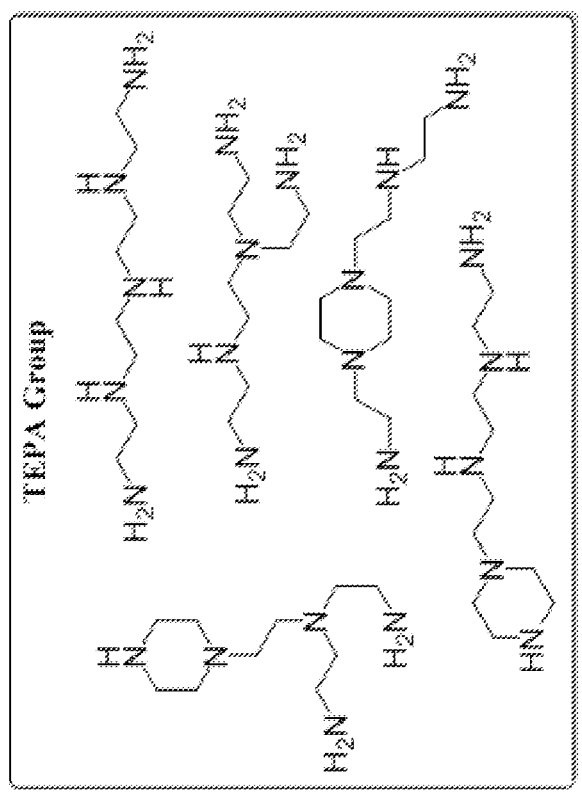

FIGS. 7A, 7B and 7C illustrate the reaction of TETA with GE followed by reaction of the intermediate with formaldehyde to form various scavengers.

In another set of experiments, vapor phase reduction tests were performed to evaluate the hydrogen sulfide scavenging efficiency of various scavengers disclosed herein. The experiments included preparing a sour fluid medium and performing the optimized vapor phase reduction evaluation. The experiments were conducted according to a modified version of ASTMD5705.

A dynamic liquid phase testing was performed to evaluate and determine a blank and $H_2S$ concentration of the liquid medium. The procedures for the test included purging a sample of hydrocarbon liquid medium with hydrogen sulfide to a determined amount of $H_2$. Then, about 100 mL of the fluid medium was placed and sealed in a glass bottle with corresponding dosage rates. The fluid included a liquid medium comprising a hydrocarbon medium (about 100%). After preparation, the samples were heated to about 70° C. with agitation in a dynamic box for about 30 minutes. The samples were measured for remaining hydrogen sulfide content by using cadmium chloride titration.

In accordance with certain tests, the hydrogen sulfide content was measured in the vapor phase. A known amount of hydrocarbon was purged with a target concentration of hydrogen sulfide gas, which was then transferred to a glass vessel with a selected scavenger and dosage rate. The glass vessel was then heated in a dynamic box for a time period based on retention time in the field. A Gastec tube was then used to measure head space $H_2S$ level. Different groups of reactive chemistries were dosed 10:1 and the results are outlined in the Table 1.

TABLE 1

| Experimental H2S Scavengers | Initial ppm | Final ppm | % H2S Removed |
| --- | --- | --- | --- |
| 1. Blank | 1000 | 1000 | 0 |
| 2. DETA and 3 mole n-butylglycidylether hemiformal in EGMBE, 87.20% | 1000 | 500 | 50 |
| 3. DETA and 3 mole isopropylglycidylether hemiformal in EGMBE, 82.50% | 1000 | 400 | 60 |
| 4. DETA and 3 mole phenylglycidylether hemiformal in EGMBE, 87.50% | 1000 | 800 | 20 |
| 5. TETA and 4 mole phenylglycidylether hemiformal in EGMBE, 86.12% | 1000 | 800 | 20 |
| 6. TETA and 4 mole n-butylglycidylether hemiformal in EGMBE, 89.30% | 1000 | 50 | 95 |

TABLE 1-continued

| Experimental H2S Scavengers | Initial ppm | Final ppm | % H2S Removed |
| --- | --- | --- | --- |
| 7. TETA and 4 mole isopropylglycidylether hemiformal in EGMBE, 89.50% | 1000 | 100 | 90 |
| 8. EDA and 3 mole isopropylglycidylether hemiformal in EGMBE, 88.50% | 1000 | 100 | 90 |
| 9. EDA and 3 mole n-butylglycidylether hemiformal in EGMBE, 79.87% | 1000 | 350 | 65 |
| 10. EDA and 2 mole ethylene oxide hemiformal, no solvent | 1000 | 650 | 35 |
| 11. EDA and 2 mole propylene oxide hemiformal, no solvent | 1000 | 700 | 30 |
| 12. EDA and 4 mole ethylene oxide hemiformal, no solvent | 1000 | 75 | 92.5 |
| 13. EDA and 4 mole propylene oxide hemiformal, no solvent | 1000 | 100 | 90 |
| 14. DETA and 4 mole ethylene oxide hemiformal, no solvent | 1000 | 600 | 40 |
| 15. DETA and 4 mole propylene oxide hemiformal, no solvent | 1000 | 200 | 80 |
| 16. TETA and 4 mole ethylene oxide hemiformal, no solvent | 1000 | 600 | 40 |
| 17. TETA and 4 mole propylene oxide hemiformal, no solvent | 1000 | 200 | 80 |
| 18. Blank 2 | 1000 | 1000 | 0 |

Corresponding chemical structures for the compositions listed in Table 1 are as follows:

1. N/A

2.

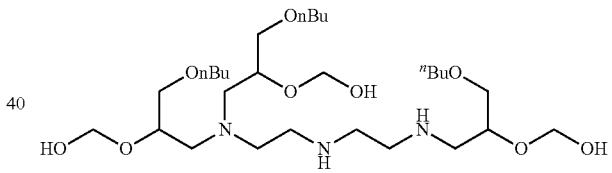

3.

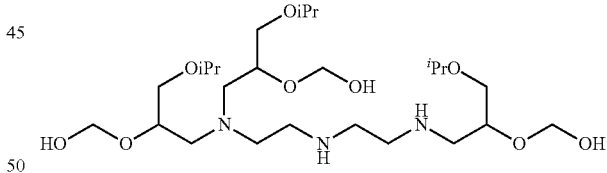

4.

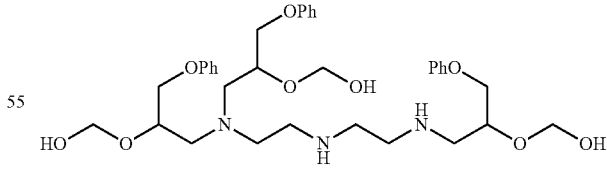

5.

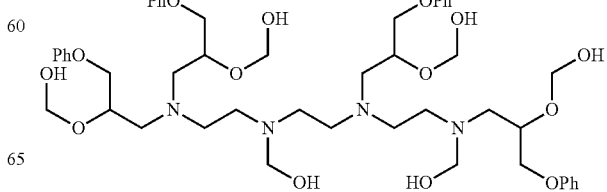

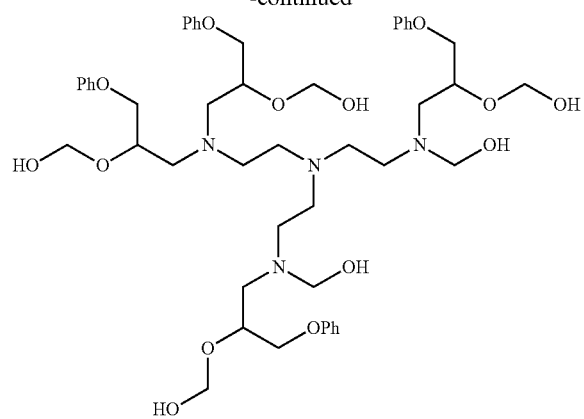
6.
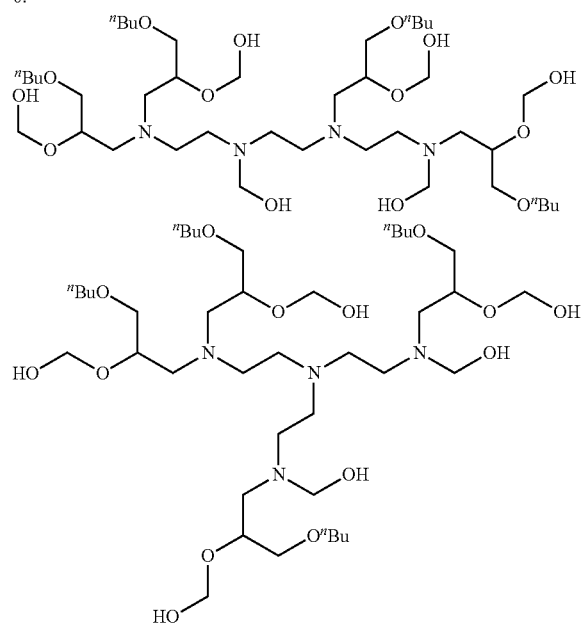
7.
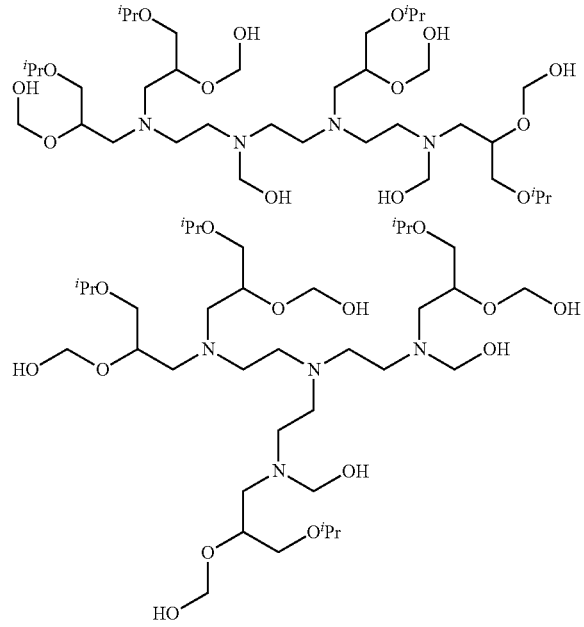
8.
9.
10.
11.
12.
13.
14.
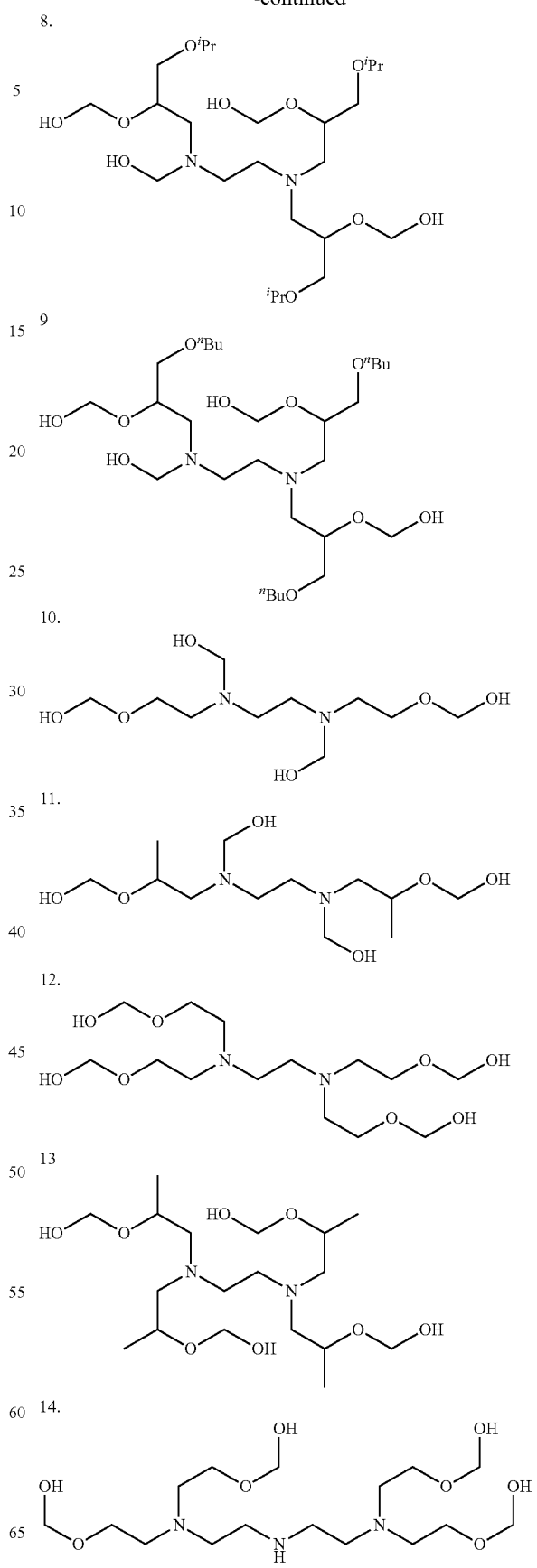

-continued

15.

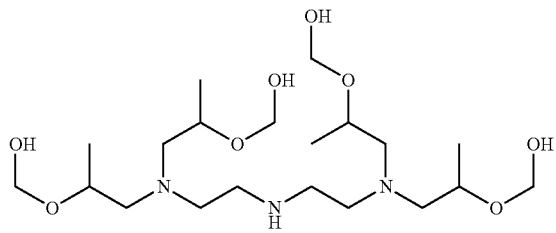

16.

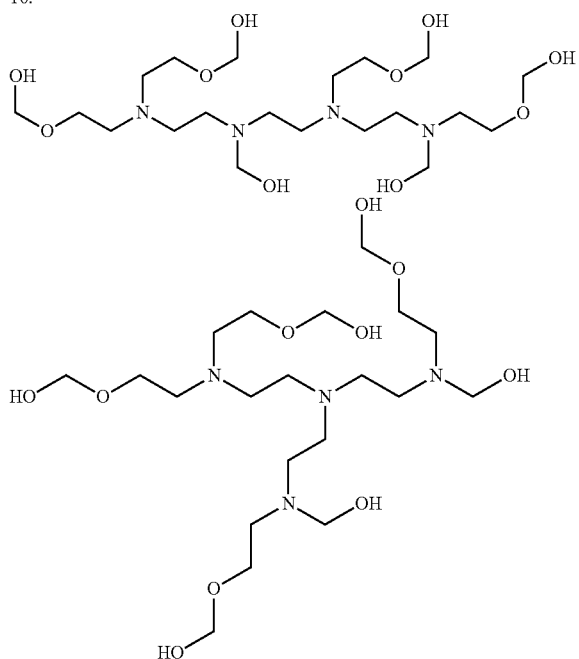

17.

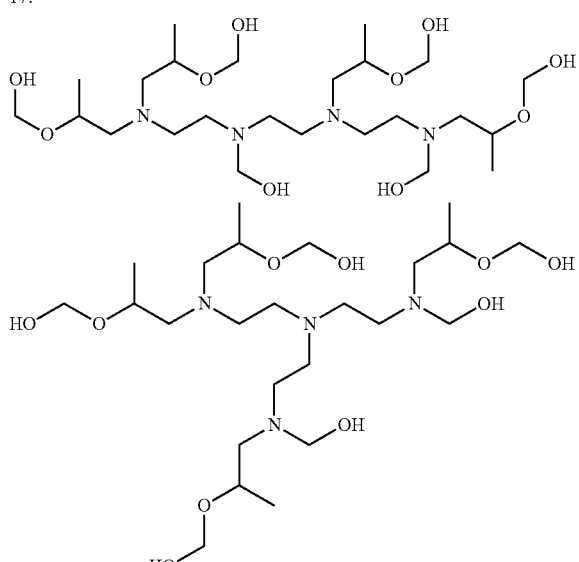

18. N/A

The compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a scavenger" is intended to include "at least one scavenger" or "one or more scavengers."

Any composition disclosed herein may comprise, consist of or consist essentially of any of the compounds/components disclosed herein. In accordance with the present disclosure, the phrases "consist essentially of," "consists essentially of," "consisting essentially of," and the like limit the scope of a claim to the specified materials or steps and those materials or steps that do not materially affect the basic and novel characteristic(s) of the claimed invention.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A composition comprising at least one hydrogen sulfide scavenger comprising a structure selected from the group consisting of:

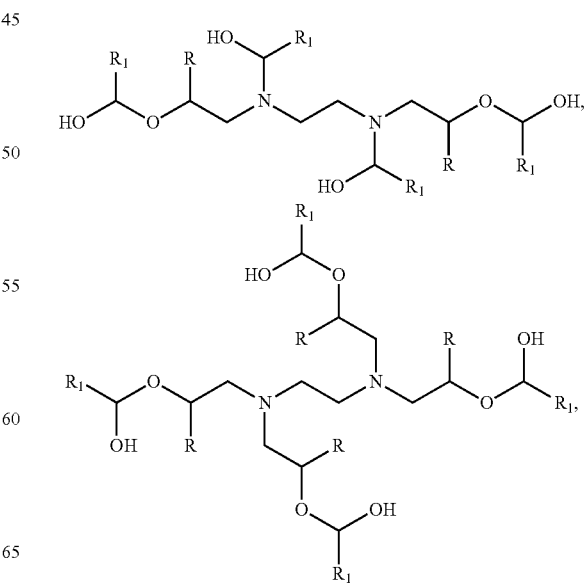

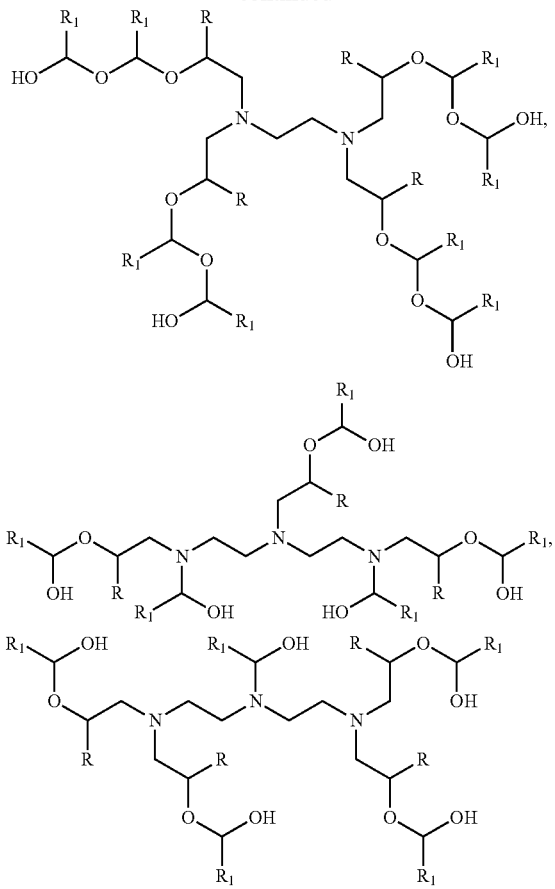

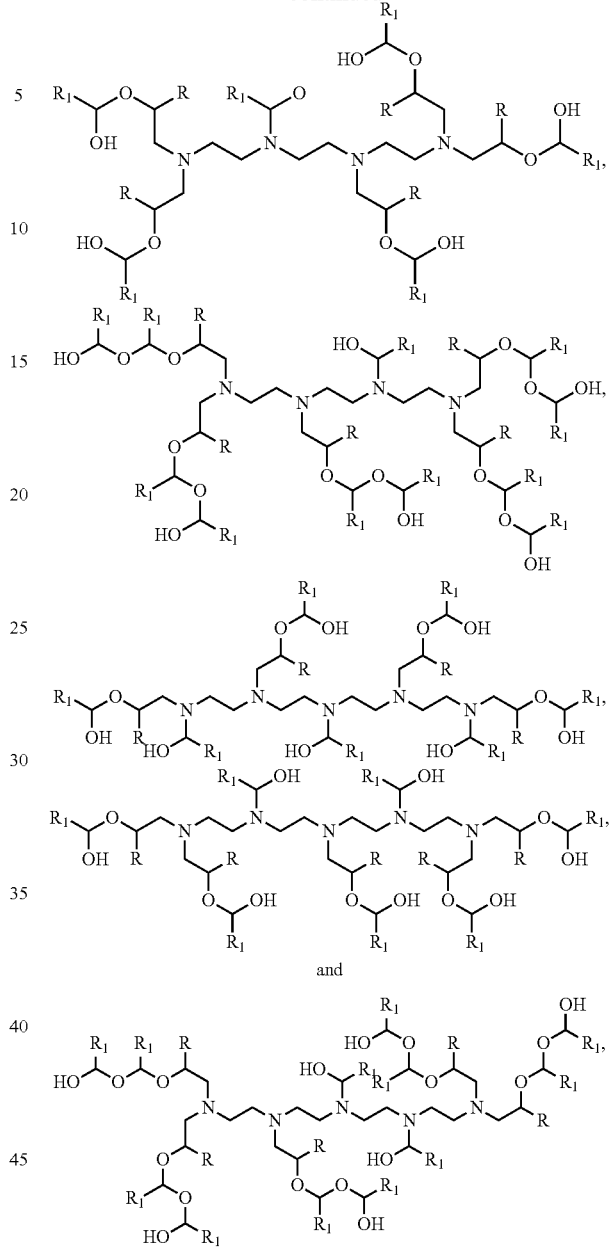

wherein each R is independently selected from a hydrogen, methyl, ethyl, propyl, and/or $CH_2OR_{10}$, where $R_{10}$=H, methyl, ethyl, propyl, isopropyl, butyl, phenyl, or benzyl; and wherein each $R_1$ is independently selected from a hydrogen or methyl.

2. The composition of claim 1, wherein the composition further comprises a stream.

3. The composition of claim 2, wherein the stream is aqueous, gaseous, organic, or any combination thereof.

4. The composition of claim 1, wherein the composition is anhydrous.

5. The composition of claim 1, wherein the composition comprises an aqueous solvent or an organic solvent.

* * * * *